United States Patent
Thompson

(10) Patent No.: US 12,134,770 B1
(45) Date of Patent: Nov. 5, 2024

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 18/582,361

(22) Filed: Feb. 20, 2024

(51) Int. Cl.
| | | |
|---|---|---|
| *C12N 15/113* | (2010.01) | |
| *A61K 35/76* | (2015.01) | |
| *C12N 15/86* | (2006.01) | |

(52) U.S. Cl.
CPC .......... *C12N 15/1138* (2013.01); *A61K 35/76* (2013.01); *C12N 15/86* (2013.01); *C12N 2310/141* (2013.01); *C12N 2750/14143* (2013.01)

(58) Field of Classification Search
None
See application file for complete search history.

(56) References Cited

PUBLICATIONS

Bahi et al. Lentiviral-mediated up-regulation of Let-7d microRNA decreases Alcohol Intake through Down-regulation the dopamine D3 receptor. European Neuropsychopharmacology, 2020. 37:70-81.*

Poi et al. miRNA Cassettes in Viral Vectors: Problems and Solutions. Biochimica et Biophysica Acta, 2011. 732-745.*

Lanza et al. Genetic Suppression of the Dopamine D3 Receptor in Striatal D1 Cells Reduces the Development of L-DOPA-induced Dyskinesia. Experimental Neurology, 2021. 336:113534, 9 pages.*

Shinohara et al. Dopamine D1 Receptor Subtype Mediates Acute Stress-Induced Dendritic Growth In Excitatory Neurons of the Medial Prefrontal Cortex and Contributes to Suppression of Stress Susceptibility in Mice. Molecular Psychiatry, 2018. 23:1717-1730 with Supplement.*

* cited by examiner

*Primary Examiner* — Christopher M Babic
*Assistant Examiner* — Kimberly A Aron
(74) *Attorney, Agent, or Firm* — Gowling WLG (Canada) LLP

(57) ABSTRACT

Embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for a target biomolecule and the miRNA can cause a decrease in bioavailability of the target biomolecule within a subject that is administered the one or more compositions. In some embodiments of the present disclosure, the target biomolecule is a dopamine receptor. In some embodiments of the present disclosure, the target biomolecule is a dopamine receptor such as the D1 dopamine receptor, such as the D2 dopamine receptor, such as the D3 dopamine receptor, or such as the D4 dopamine receptor.

15 Claims, No Drawings

Specification includes a Sequence Listing.

COMPOSITION FOR REGULATING PRODUCTION OF INTERFERING RIBONUCLEIC ACID

This application contains a Sequence Listing electronically submitted via Patent Center to the United States Patent and Trademark Office as an XML Document file entitled "A8149443US-Sequence Listing.xml" created on 2024 Feb. 12 and having a size of 41,724 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and consequently, the production of interfering RNA that will suppress dopamine receptor expression.

BACKGROUND

Bioactive molecules, including dopamine receptors, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a dopamine receptor. In some embodiments of the present disclosure, the target biomolecule is a dopamine receptor such as the D1 dopamine receptor. In some embodiments of the present disclosure, the target biomolecule is a dopamine receptor such as the D2 dopamine receptor. In some embodiments of the present disclosure, the target biomolecule is a dopamine receptor such as the D3 dopamine receptor. In some embodiments of the present disclosure, the target biomolecule is a dopamine receptor such as the D4 dopamine receptor.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets the mRNA of the D1 dopamine receptor.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets the mRNA of the D2 dopamine receptor.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets the mRNA of the D3 dopamine receptor.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets the mRNA of the D4 dopamine receptor.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, or SEQ ID NO. 5, to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence the mRNA of a target biomolecule, for example the D1 dopamine receptor. A first approach utilizes gene vectors containing nucleotide sequences for increasing the endogenous production of one or more sequences of miRNA, which are complete or partial sequences and/or combinations thereof, that target and silence the mRNA of the D1 dopamine receptor, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example the D2 dopamine receptor. A first approach utilizes gene vectors containing nucleotide sequences for increasing the endogenous production of one or more sequences of miRNA, which are complete or partial sequences and/or combinations thereof, that target and silence the mRNA of the D2 dopamine receptor, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example the D3 dopamine receptor. A first approach utilizes gene vectors containing nucleotide sequences for increasing the endogenous production of one or more sequences of miRNA, which are complete or partial sequences and/or combinations thereof, that target and silence the mRNA of the D3 dopamine receptor, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example the D4 dopamine receptor. A first approach utilizes gene vectors containing nucleotide sequences for increasing the endogenous production of one or more sequences of miRNA, which are complete or partial sequences and/or combinations thereof, that target and silence the mRNA of the D4 dopamine receptor, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred compositions, methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more biological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a dopamine receptor that is found within a subject. A biomolecule may be endogenous or exogenous to a subject and when bioavailable the biomolecule may inhibit or stimulate a biological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is the D1 dopamine receptor.

In some embodiments of the present disclosure, the target biomolecule is the D2 dopamine receptor.

In some embodiments of the present disclosure, the target biomolecule is the D3 dopamine receptor.

In some embodiments of the present disclosure, the target biomolecule is the D4 dopamine receptor.

In some embodiments of the present disclosure, the insert comprises one or more nucleotide sequences that each encode for one or more miRNA sequences that may be complimentary to and degrade, or cause degradation of, mRNA of the target biomolecule.

Some embodiments of the present disclosure relate to a composition that can be administered to a subject with a condition that results, directly or indirectly, from the dysregulated production of a biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complimentary to and degrade, or cause degradation of, one biomolecule, such as the D1 dopamine receptor, the D2 dopamine receptor, the D3 dopamine receptor, or the D4 dopamine receptor. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complimentary to and degrade, or cause degradation of, or inactivate, or cause inactivation of, one biomolecule, such as the D1 dopamine receptor, the D2 dopamine receptor, the D3 dopamine receptor, or the D4 dopamine receptor.

In some embodiments of the present disclosure, the delivery vehicle of the RP used for gene therapy may be a vector that comprises a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus Dependoparvovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1\times10^{16}$ $TCID_{50}$/kg (50% tissue culture infective dose per kilogram of the patient's body mass). In some embodiments of the present disclosure, the therapeutically effective amount of the composition that is administered to the patient is about $1\times10^{13}$ $TCID_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1\times10^{16}$ TCP/kg.

Some embodiments of the present disclosure relate to an adeno-associated virus (AAV) genome consisting of a RP that when operable inside a target cell will cause the target cell to produce a miRNA sequence that downregulates production of a biomolecule, with examples being the D1 dopamine receptor, the D2 dopamine receptor, the D3 dopamine receptor, or the D4 dopamine receptor. The RP is comprised of AAV2 inverted terminal repeats (ITRs), a composite CASI promoter, a human growth hormone (HGH) signal peptide followed by a miRNA expression cassette containing up to six different miRNAs targeting the D1 dopamine receptor, the D2 dopamine receptor, the D3 dopamine receptor, or the D4 dopamine receptor, followed by a Woodchuck Hepatitis Virus post-transcriptional regulatory element (WPRE) and a Simian virus 40 (SV40) polyadenylation (polyA) signal.

SEQ ID NO. 1 (backbone sequence No. 1):
5'

AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTAAGCTTATCGATACCGTCGAGATCTAACTTGTTTATTGCAGCTTAT

AATGGTTACAAATAAAGCAATAGCATCACAAATTTCACAAATAAAGCAT

TTTTTTCACTGCATTCTAGTTGTGGTTTGTCCAAACTCATCAATGTATC

TTATCATGTCTGGATCTCGACCTCGACTAGAGCATGGCTACGTAGATAA

GTAGCATGGCGGGTTAATCATTAACTACAAGGAACCCCTAGTGATGGAG

TTGGCCACTCCCTCTCTGCGCGCTCGCTCGCTCACTGAGGCCGGGCGAC

CAAAGGTCGCCCGACGCCCGGGCTTTGCCCGGGCGGCCTCAGTGAGCGA

GCGAGCGCGCAGCTGGCGTAATAGCGAAGAGGCCCGCACCGATCGCCCT

TCCCAACAGTTGCGCAGCCTGAATGGCGAATGGCGATTCCGTTGCAATG

GCTGGCGGTAATATTGTTCTGGATATTACCAGCAAGGCCGATAGTTTGA

GTTCTTCTACTCAGGCAAGTGATGTTATTACTAATCAAAGAAGTATTGC

GACAACGGTTAATTTGCGTGATGGACAGACTCTTTTACTCGGTGGCCTC

ACTGATTATAAAAACACTTCTCAGGATTCTGGCGTACCGTTCCTGTCTA

AAATCCCTTTAATCGGCCTCCTGTTTAGCTCCCGCTCTGATTCTAACGA

GGAAAGCACGTTATACGTGCTCGTCAAAGCAACCATAGTACGCGCCCTG

TAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGG

GCTCCCTTTAGGGTTCCGATTTAGTGCTTTACGGCACCTCGACCCCAAA

AAACTTGATTAGGGTGATGGTTCACGTAGTGGGCCATCGCCCTGATAGA

CGGTTTTTCGCCCTTTGACGTTGGAGTCCACGTTCTTTAATAGTGGACT

CTTGTTCCAAACTGGAACAACACTCAACCCTATCTCGGTCTATTCTTTT

GATTTATAAGGGATTTTGCCGATTTCGGCCTATTGGTTAAAAAATGAGC

TGATTTAACAAAAATTTAACGCGAATTTTAACAAAATATTAACGTTTAC

AATTTAAATATTTGCTTATACAATCTTCCTGTTTTTGGGGCTTTTCTGA

TTATCAACCGGGGTACATATGATTGACATGCTAGTTTTACGATTACCGT

TCATCGATTCTCTTGTTTGCTCCAGACTCTCAGGCAATGACCTGATAGC

CTTTGTAGAGACCTCTCAAAAATAGCTACCCTCTCCGGCATGAATTTAT

CAGCTAGAACGGTTGAATATCATATTGATGGTGATTTGACTGTCTCCGG

CCTTTCTCACCCGTTTGAATCTTTACCTACACATTACTCAGGCATTGCA

TTTAAAATATATGAGGGTTCTAAAAATTTTTATCCTTGCGTTGAAATAA

AGGCTTCTCCCGCAAAAGTATTACAGGGTCATAATGTTTTTGGTACAAC

CGATTTAGCTTTATGCTCTGAGGCTTTATTGCTTAATTTTGCTAATTCT

TTGCCTTGCCTGTATGATTTATTGGATGTTGGAATTCCTGATGCGGTAT

TTTCTCCTTACGCATCTGTGCGGTATTTCACACCGCATATGGTGCACTC

TCAGTACAATCTGCTCTGATGCCGCATAGTTAAGCCAGCCCCGACACCC

GCCAACACCCGCTGACGCGCCCTGACGGGCTTGTCTGCTCCCGGCATCC

GCTTACAGACAAGCTGTGACCGTCTCCGGGAGCTGCATGTGTCAGAGGT

TTTCACCGTCATCACCGAAACGCGCGAGACGAAAGGGCCTCGTGATACG

CCTATTTTTATAGGTTAATGTCATGATAATAATGGTTTCTTAGACGTCA

GGTGGCACTTTTCGGGGAAATGTGCGCGGAACCCCTATTTGTTTATTTT

TCTAAATACATTCAAATATGTATCCGCTCATGAGACAATAACCCTGATA

AATGCTTCAATAATATTGAAAAAGGAAGAGTATGAGTATTCAACATTTC

CGTGTCGCCCTTATTCCCTTTTTTGCGGCATTTTGCCTTCCTGTTTTTG

CTCACCCAGAAACGCTGGTGAAAGTAAAAGATGCTGAAGATCAGTTGGG

TGCACGAGTGGGTTACATCGAACTGGATCTCAACAGCGGTAAGATCCTT

GAGAGTTTTCGCCCCGAAGAACGTTTTCCAATGATGAGCACTTTTAAAG

TTCTGCTATGTGGCGCGGTATTATCCCGTATTGACGCCGGGCAAGAGCA

ACTCGGTCGCCGCATACACTATTCTCAGAATGACTTGGTTGAGTACTCA

CCAGTCACAGAAAAGCATCTTACGGATGGCATGACAGTAAGAGAATTAT

GCAGTGCTGCCATAACCATGAGTGATAACACTGCGGCCAACTTACTTCT

GACAACGATCGGAGGACCGAAGGAGCTAACCGCTTTTTTGCACAACATG

GGGGATCATGTAACTCGCCTTGATCGTTGGGAACCGGAGCTGAATGAAG

CCATACCAAACGACGAGCGTGACACCACGATGCCTGTAGCAATGGCAAC

AACGTTGCGCAAACTATTAACTGGCGAACTACTTACTCTAGCTTCCCGG

CAACAATTAATAGACTGGATGGAGGCGGATAAAGTTGCAGGACCACTTC

TGCGCTCGGCCCTTCCGGCTGGCTGGTTTATTGCTGATAAATCTGGAGC

-continued

CGGTGAGCGTGGGTCTCGCGGTATCATTGCAGCACTGGGGCCAGATGGT
AAGCCCTCCCGTATCGTAGTTATCTACACGACGGGGAGTCAGGCAACTA
TGGATGAACGAAATAGACAGATCGCTGAGATAGGTGCCTCACTGATTAA
GCATTGGTAACTGTCAGACCAAGTTTACTCATATATACTTTAGATTGAT
TTAAAACTTCATTTTTAATTTAAAAGGATCTAGGTGAAGATCCTTTTTG
ATAATCTCATGACCAAAATCCCTTAACGTGAGTTTTCGTTCCACTGAGC
GTCAGACCCCGTAGAAAAGATCAAAGGATCTTCTTGAGATCCTTTTTTT
CTGCGCGTAATCTGCTGCTTGCAAACAAAAAAACCACCGCTACCAGCGG
TGGTTTGTTTGCCGGATCAAGAGCTACCAACTCTTTTTCCGAAGGTAAC
TGGCTTCAGCAGAGCGCAGATACCAAATACTGTCCTTCTAGTGTAGCCG
TAGTTAGGCCACCACTTCAAGAACTCTGTAGCACCGCCTACATACCTCG
CTCTGCTAATCCTGTTACCAGTGGCTGCTGCCAGTGGCGATAAGTCGTG
TCTTACCGGGTTGGACTCAAGACGATAGTTACCGGATAAGGCGCAGCGG
TCGGGCTGAACGGGGGGTTCGTGCACACAGCCCAGCTTGGAGCGAACGA
CCTACACCGAACTGAGATACCTACAGCGTGAGCTATGAGAAAGCGCCAC
GCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATC
TTTATAGTCCTGTCGGGTTTCGCCACCTCTGACTTGAGCGTCGATTTTT
GTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCT
TTCCTGCGTTATCCCCTGATTCTGTGGATAACCGTATTACCGCCTTTGA
GTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCG
CGCGTTGGCCGATTCATTAATGCAGCAGCTGCGCGCTCGCTCGCTCACT
GAGGCCGCCCGGGCAAAGCCCGGGCGTCGGGCGACCTTTGGTCGCCCGG
CCTCAGTGAGCGAGCGAGCGCGCAGAGAGGGAGTGGCCAACTCCATCAC
TAGGGGTTCCTTGTAGTTAATGATTAACCCGCCATGCTACTTATCTACG
TAGCCATGCTCTAGGACATTGATTATTGACTAGTGGAGTTCCGCGTTAC
ATAACTTACGGTAAATGGCCCGCCTGGCTGACCGCCCAACGACCCCCGC
CCATTGACGTCAATAATGACGTATGTTCCCATAGTAACGCCAATAGGGA
CTTTCCATTGACGTCAATGGGTGGAGTATTTACGGTAAACTGCCCACTT
GGCAGTACATCAAGTGTATCATATGCCAAGTACGCCCCCTATTGACGTC
AATGACGGTAAATGGCCCGCCTGGCATTATGCCCAGTACATGACCTTAT
GGGACTTTCCTACTTGGCAGTACATCTACGTATTAGTCATCGCTATTAC
CATGGTCGAGGTGAGCCCCACGTTCTGCTTCACTCTCCCCATCTCCCCC
CCCTCCCCACCCCCAATTTTGTATTTATTTATTTTTAATTATTTTGTG
CAGCGATGGGGGCGGGGGGGGGGGGCGCGCGCCAGGCGGGGCGGGG
GGGGGCGAGGGGCGGGGCGGGGCGAGGCGGAGAGGTGCGGCGGCAGCCA
ATCAGAGCGGCGCGCTCCGAAAGTTTCCTTTTATGGCGAGGCGGCGGCG
GCGGCGGCCCTATAAAAAGCGAAGCGCGCGGCGGGCGGGAGTCGCTGCG
CGCTGCCTTCGCCCCGTGCCCCGCTCCGCCGCCGCCTCGCGCCGCCCGC

-continued

CCCGGCTCTGACTGACCGCGTTACTAAAACAGGTAAGTCCGGCCTCCGC
GCCGGGTTTTGGCGCCTCCCGCGGGCGCCCCCCTCCTCACGGCGAGCGC
TGCCACGTCAGACGAAGGGCGCAGCGAGCGTCCTGATCCTTCCGCCCGG
ACGCTCAGGACAGCGGCCCGCTGCTCATAAGACTCGGCCTTAGAACCCC
AGTATCAGCAGAAGGACATTTTAGGACGGGACTTGGGTGACTCTAGGGC
ACTGGTTTTCTTTCCAGAGAGCGGAACAGGCGAGGAAAAGTAGTCCCTT
CTCGGCGATTCTGCGGAGGGATCTCCGTGGGGCGGTGAACGCCGATGAT
GCCTCTACTAACCATGTTCATGTTTTCTTTTTTTTTCTACAGGTCCTGG
GTGACGAACAGGGTACC

3'

SEQ ID NO. 2 (miRNA expression cassette No. 2 - D1 dopamine receptor):

5'
GCCACCATGGCCACCGGCTCTCGCACAAGCCTGCTGCTGGCTTTCGGAC
TGCTGTGCCTGCCTTGGCTCCAGGAGGGCTCCGCCGCTAGCATCGATAC
CGTCGCTATGTGCTGGAGGCTTGCTGAAGGCTGTATGCTGTATCAATGG
TTTGTCCGCCAGGCGTTTTGGCCTCTGACTGACGCCTGGCGGAAACCAT
TGATACAGGACACAAGGCCTGTTACTAGCACTCACATGGAACAAATGGC
CTCTAGCCTGGAGGCTTGCTGAAGGCTGTATGCTGAAATAATCGGGATT
TCAGGCTGCGTTTTGGCCTCTGACTGACGCAGCCTGAACCCGATTATTT
CAGGACACAAGGCCTGTTACTAGCACTCACATGGAACAAATGGCCTCTA
GCCTGGAGGCTTGCTGAAGGCTGTATGCTGATTCTTTGCTAAAATGCTG
CCGCGTTTTGGCCTCTGACTGACGCGGCAGCATTAGCAAAGAATCAGGA
CACAAGGCCTGTTACTAGCACTCACATGGAACAAATGGCCTCTCTAGAA
T

3'

SEQ ID NO. 3 (miRNA expression cassette No. 3 - D2 dopamine receptor):

5'
GCCACCATGGCCACCGGCTCTCGCACAAGCCTGCTGCTGGCTTTCGGAC
TGCTGTGCCTGCCTTGGCTCCAGGAGGGCTCCGCCGCTAGCATCGATAC
CGTCGCTATGTGCTGGAGGCTTGCTGAAGGCTGTATGCTGAGATAGTTG
GTTGGGTGGTCTGCGTTTTGGCCTCTGACTGACGCAGACCACCACCAAC
TATCTCAGGACACAAGGCCTGTTACTAGCACTCACATGGAACAAATGGC
CTCTAGCCTGGAGGCTTGCTGAAGGCTGTATGCTGTGCTAATCATCATA
CGGTCACGCGTTTTGGCCTCTGACTGACGCGTGACCGTGATGATTAGCA
CAGGACACAAGGCCTGTTACTAGCACTCACATGGAACAAATGGCCTCTA
GCCTGGAGGCTTGCTGAAGGCTGTATGCTGACATAGCCCAGAACCAGGT
AAACGTTTTGGCCTCTGACTGACGTTTACCTGGCTGGGCTATGTCAGGA

CACAAGGCCTGTTACTAGCACTCACATGGAACAAATGGCCTCTCTAGAA

T

3'

SEQ ID NO. 4 (miRNA expression cassette No. 4 -
D3 dopamine receptor):
5'

GCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATAC

CGTCGCTATGTGCTGGAGGCTTGCTGAAGGCTGTATGCTGAGATAGTTG

GTTGGGTGGTCTGCGTTTTGGCCTCTGACTGACGCAGACCACCACCAAC

TATCTCAGGACACAAGGCCTGTTACTAGCACTCACATGGAACAAATGGC

CTCTAGCCTGGAGGCTTGCTGAAGGCTGTATGCTGTTTCTTCGCGTTGT

TCAGTTCGCGTTTTGGCCTCTGACTGACGCGAACTGAAACGCGAAGAAA

CAGGACACAAGGCCTGTTACTAGCACTCACATGGAACAAATGGCCTCTA

GCCTGGAGGCTTGCTGAAGGCTGTATGCTGTTTCTTCGCGTAATTCAGT

TCGCGTTTTGGCCTCTGACTGACGCGAACTGAAACGCGAAGAAACAGGA

CACAAGGCCTGTTACTAGCACTCACATGGAACAAATGGCCTCTCTAGAA

T

3'

SEQ ID NO. 5 (miRNA expression cassette No. 5 -
D4 dopamine receptor):
5'

GCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATAC

CGTCGCTATGTGCTGGAGGCTTGCTGAAGGCTGTATGCTGATAAATCAC

CGTGGGTTCAGCGCGTTTTGGCCTCTGACTGACGCGCTGAACCCGGTGA

TTTATCAGGACACAAGGCCTGTTACTAGCACTCACATGGAACAAATGGC

CTCTAGCCTGGAGGCTTGCTGAAGGCTGTATGCTGATAAATCACCGATG

GTTCAGCGCGTTTTGGCCTCTGACTGACGCGCTGAACCCGGTGATTTAT

CAGGACACAAGGCCTGTTACTAGCACTCACATGGAACAAATGGCCTCTA

GCCTGGAGGCTTGCTGAAGGCTGTATGCTGATAAATCACCGAAGGTTCA

GCGCGTTTTGGCCTCTGACTGACGCGCTGAACCCGGTGATTTATCAGGA

CACAAGGCCTGTTACTAGCACTCACATGGAACAAATGGCCTCTCTAGAA

T

3'

SEQ ID NO. 6 = SEQ ID NO. 1 + SEQ ID NO. 2
5'

AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTAAGCTTATCGATACCGTCGAGATCTAACTTGTTTATTGCAGCTTAT

AATGGTTACAAATAAAGCAATAGCATCACAAATTTCACAAATAAAGCAT

TTTTTTCACTGCATTCTAGTTGTGGTTTGTCCAAACTCATCAATGTATC

TTATCATGTCTGGATCTCGACCTCGACTAGAGCATGGCTACGTAGATAA

GTAGCATGGCGGGTTAATCATTAACTACAAGGAACCCCTAGTGATGGAG

TTGGCCACTCCCTCTCTGCGCGCTCGCTCGCTCACTGAGGCCGGGCGAC

CAAAGGTCGCCCGACGCCCGGGCTTTGCCCGGGCGGCCTCAGTGAGCGA

GCGAGCGCGCAGCTGGCGTAATAGCGAAGAGGCCCGCACCGATCGCCCT

TCCCAACAGTTGCGCAGCCTGAATGGCGAATGGCGATTCCGTTGCAATG

GCTGGCGGTAATATTGTTCTGGATATTACCAGCAAGGCCGATAGTTTGA

GTTCTTCTACTCAGGCAAGTGATGTTATTACTAATCAAAGAAGTATTGC

GACAACGGTTAATTTGCGTGATGGACAGACTCTTTTACTCGGTGGCCTC

ACTGATTATAAAAACACTTCTCAGGATTCTGGCGTACCGTTCCTGTCTA

AAATCCCTTTAATCGGCCTCCTGTTTAGCTCCCGCTCTGATTCTAACGA

GGAAAGCACGTTATACGTGCTCGTCAAAGCAACCATAGTACGCGCCCTG

TAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGG

GCTCCCTTTAGGGTTCCGATTTAGTGCTTTACGGCACCTCGACCCCAAA

AAACTTGATTAGGGTGATGGTTCACGTAGTGGGCCATCGCCCTGATAGA

CGGTTTTTCGCCCTTTGACGTTGGAGTCCACGTTCTTTAATAGTGGACT

CTTGTTCCAAACTGGAACAACACTCAACCCTATCTCGGTCTATTCTTTT

GATTTATAAGGGATTTTGCCGATTTCGGCCTATTGGTTAAAAAATGAGC

TGATTTAACAAAAATTTAACGCGAATTTTAACAAAATATTAACGTTTAC

AATTTAAATATTTGCTTATACAATCTTCCTGTTTTTGGGGCTTTTCTGA

TTATCAACCGGGGTACATATGATTGACATGCTAGTTTTACGATTACCGT

TCATCGATTCTCTTGTTTGCTCCAGACTCTCAGGCAATGACCTGATAGC

CTTTGTAGAGACCTCTCAAAAATAGCTACCCTCTCCGGCATGAATTTAT

CAGCTAGAACGGTTGAATATCATATTGATGGTGATTTGACTGTCTCCGG

CCTTTCTCACCCGTTTGAATCTTTACCTACACATTACTCAGGCATTGCA

TTTAAAATATATGAGGGTTCTAAAAATTTTTATCCTTGCGTTGAAATAA

-continued

```
AGGCTTCTCCCGCAAAAGTATTACAGGGTCATAATGTTTTTGGTACAAC
CGATTTAGCTTTATGCTCTGAGGCTTTATTGCTTAATTTTGCTAATTCT
TTGCCTTGCCTGTATGATTTATTGGATGTTGGAATTCCTGATGCGGTAT
TTTCTCCTTACGCATCTGTGCGGTATTTCACACCGCATATGGTGCACTC
TCAGTACAATCTGCTCTGATGCCGCATAGTTAAGCCAGCCCCGACACCC
GCCAACACCCGCTGACGCGCCCTGACGGGCTTGTCTGCTCCCGGCATCC
GCTTACAGACAAGCTGTGACCGTCTCCGGGAGCTGCATGTGTCAGAGGT
TTTCACCGTCATCACCGAAACGCGCGAGACGAAAGGGCCTCGTGATACG
CCTATTTTTATAGGTTAATGTCATGATAATAATGGTTTCTTAGACGTCA
GGTGGCACTTTTCGGGGAAATGTGCGCGGAACCCCTATTTGTTTATTTT
TCTAAATACATTCAAATATGTATCCGCTCATGAGACAATAACCCTGATA
AATGCTTCAATAATATTGAAAAGGAAGAGTATGAGTATTCAACATTTC
CGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGG
TGCACGAGTGGGTTACATCGAACTGGATCTCAACAGCGGTAAGATCCTT
GAGAGTTTTCGCCCCGAAGAACGTTTTCCAATGATGAGCACTTTTAAAG
TTCTGCTATGTGGCGCGGTATTATCCCGTATTGACGCCGGGCAAGAGCA
ACTCGGTCGCCGCATACACTATTCTCAGAATGACTTGGTTGAGTACTCA
CCAGTCACAGAAAAGCATCTTACGGATGGCATGACAGTAAGAGAATTAT
GCAGTGCTGCCATAACCATGAGTGATAACACTGCGGCCAACTTACTTCT
GACAACGATCGGAGGACCGAAGGAGCTAACCGCTTTTTTGCACAACATG
GGGGATCATGTAACTCGCCTTGATCGTTGGGAACCGGAGCTGAATGAAG
CCATACCAAACGACGAGCGTGACACCACGATGCCTGTAGCAATGGCAAC
AACGTTGCGCAAACTATTAACTGGCGAACTACTTACTCTAGCTTCCCGG
CAACAATTAATAGACTGGATGGAGGCGGATAAAGTTGCAGGACCACTTC
TGCGCTCGGCCCTTCCGGCTGGCTGGTTTATTGCTGATAAATCTGGAGC
CGGTGAGCGTGGGTCTCGCGGTATCATTGCAGCACTGGGGCCAGATGGT
AAGCCCTCCCGTATCGTAGTTATCTACACGACGGGGAGTCAGGCAACTA
TGGATGAACGAAATAGACAGATCGCTGAGATAGGTGCCTCACTGATTAA
GCATTGGTAACTGTCAGACCAAGTTTACTCATATATACTTTAGATTGAT
TTAAAACTTCATTTTTAATTTAAAAGGATCTAGGTGAAGATCCTTTTTG
ATAATCTCATGACCAAAATCCCTTAACGTGAGTTTTCGTTCCACTGAGC
GTCAGACCCCGTAGAAAAGATCAAAGGATCTTCTTGAGATCCTTTTTTT
CTGCGCGTAATCTGCTGCTTGCAAACAAAAAAACCACCGCTACCAGCGG
TGGTTTGTTTGCCGGATCAAGAGCTACCAACTCTTTTTCCGAAGGTAAC
TGGCTTCAGCAGAGCGCAGATACCAAATACTGTCCTTCTAGTGTAGCCG
TAGTTAGGCCACCACTTCAAGAACTCTGTAGCACCGCCTACATACCTCG
CTCTGCTAATCCTGTTACCAGTGGCTGCTGCCAGTGGCGATAAGTCGTG
TCTTACCGGGTTGGACTCAAGACGATAGTTACCGGATAAGGCGCAGCGG
TCGGGCTGAACGGGGGGTTCGTGCACACAGCCCAGCTTGGAGCGAACGA
CCTACACCGAACTGAGATACCTACAGCGTGAGCTATGAGAAAGCGCCAC
GCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATC
TTTATAGTCCTGTCGGGTTTCGCCACCTCTGACTTGAGCGTCGATTTTT
GTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCT
TTCCTGCGTTATCCCCTGATTCTGTGGATAACCGTATTACCGCCTTTGA
GTGAGCTGATACCGCTCGCCGCAGCCGAACGACCGAGCGCAGCGAGTCA
GTGAGCGAGGAAGCGGAAGAGCGCCCAATACGCAAACCGCCTCTCCCCG
CGCGTTGGCCGATTCATTAATGCAGCAGCTGCGCGCTCGCTCGCTCACT
GAGGCCGCCCGGGCAAAGCCCGGGCGTCGGGCGACCTTTGGTCGCCCGG
CCTCAGTGAGCGAGCGAGCGCGCAGAGAGGGAGTGGCCAACTCCATCAC
TAGGGGTTCCTTGTAGTTAATGATTAACCCGCCATGCTACTTATCTACG
TAGCCATGCTCTAGGACATTGATTATTGACTAGTGGAGTTCCGCGTTAC
ATAACTTACGGTAAATGGCCCGCCTGGCTGACCGCCCAACGACCCCCGC
CCATTGACGTCAATAATGACGTATGTTCCCATAGTAACGCCAATAGGGA
CTTTTCCATTGACGTCAATGGGTGGAGTATTTACGGTAAACTGCCCACTT
GGCAGTACATCAAGTGTATCATATGCCAAGTACGCCCCCTATTGACGTC
AATGACGGTAAATGGCCCGCCTGGCATTATGCCCAGTACATGACCTTAT
GGGACTTTCCTACTTGGCAGTACATCTACGTATTAGTCATCGCTATTAC
CATGGTCGAGGTGAGCCCCACGTTCTGCTTCACTCTCCCCATCTCCCCC
CCCTCCCCACCCCCAATTTTGTATTTATTTATTTTTTAATTATTTTGTG
CAGCGATGGGGGCGGGGGGGGGGGGGCGCGCGCCAGGCGGGGGGGG
GGGGCGAGGGGCGGGGCGGGGCGAGGCGGAGAGGTGCGGCGGCAGCCAA
TCAGAGCGGCGCGCTCCGAAAGTTTCCTTTTATGGCGAGGCGGCGGCGG
CGGCGGCCCTATAAAAAGCGAAGCGCGCGGCGGGCGGGAGTCGCTGCGC
GCTGCCTTCGCCCCGTGCCCCGCTCCGCCGCCGCCTCGCGCCGCCCGCC
CCGGCTCTGACTGACCGCGTTACTAAAACAGGTAAGTCCGGCCTCCGCG
CCGGGTTTTGGCGCCTCCCGCGGGCGCCCCCCTCCTCACGGCGAGCGCT
GCCACGTCAGACGAAGGGCGCAGCGAGCGTCCTGATCCTTCCGCCCGGA
CGCTCAGGACAGCGGCCCGCTGCTCATAAGACTCGGCCTTAGAACCCCA
GTATCAGCAGAAGGACATTTTAGGACGGGACTTGGGTGACTCTAGGGCA
CTGGTTTTCTTTCCAGAGAGCGGAACAGGCGAGGAAAAGTAGTCCCTTC
TCGGCGATTCTGCGGAGGGATCTCCGTGGGCGGTGAACGCCGATGATG
CCTCTACTAACCATGTTCATGTTTTCTTTTTTTTCTACAGGTCCTGGG
TGACGAACAGGGTACCGCCACCATGGCCACCGGCTCTCGCACAAGCCTG
CTGCTGGCTTTCGGACTGCTGTGCCTGCCTTGGCTCCAGGAGGGCTCCG
CCGCTAGCATCGATACCGTCGCTATGTGCGGAGGCTTGCTGAAGGCTG
TATGCTGTATCAATGGTTTGTCCGCCAGGCGTTTTGGCCTCTGACTGAC
GCCTGGCGGAAACCATTGATACAGGACACAAGGCCTGTTACTAGCACTC
ACATGGAACAAATGGCCTCTAGCCTGGAGGCTTGCTGAAGGCTGTATGC
```

TGAAATAATCGGGATTTCAGGCTGCGTTTTGGCCTCTGACTGACGCAGC

CTGAACCCGATTATTTCAGGACACAAGGCCTGTTACTAGCACTCACATG

GAACAAATGGCCTCTAGCCTGGAGGCTTGCTGAAGGCTGTATGCTGATT

CTTTGCTAAAATGCTGCCGCGTTTTGGCCTCTGACTGACGCGGCAGCAT

TAGCAAAGAATCAGGACACAAGGCCTGTTACTAGCACTCACATGGAACA

AATGGCCTCTCTAGAAT

3'

SEQ ID NO. 7 = SEQ ID NO. 1 + SEQ ID NO. 3
5'
AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTAAGCTTATCGATACCGTCGAGATCTAACTTGTTTATTGCAGCTTAT

AATGGTTACAAATAAAGCAATAGCATCACAAATTTCACAAATAAAGCAT

TTTTTTCACTGCATTCTAGTTGTGGTTTGTCCAAACTCATCAATGTATC

TTATCATGTCTGGATCTCGACCTCGACTAGAGCATGGCTACGTAGATAA

GTAGCATGGCGGGTTAATCATTAACTACAAGGAACCCCTAGTGATGGAG

TTGGCCACTCCCTCTCTGCGCGCTCGCTCGCTCACTGAGGCCGGGCGAC

CAAAGGTCGCCCGACGCCCGGGCTTTGCCCGGGCGGCCTCAGTGAGCGA

GCGAGCGCGCAGCTGGCGTAATAGCGAAGAGGCCCGCACCGATCGCCCT

TCCCAACAGTTGCGCAGCCTGAATGGCGAATGGCGATTCCGTTGCAATG

GCTGGCGGTAATATTGTTCTGGATATTACCAGCAAGGCCGATAGTTTGA

GTTCTTCTACTCAGGCAAGTGATGTTATTACTAATCAAAGAAGTATTGC

GACAACGGTTAATTTGCGTGATGGACAGACTCTTTTACTCGGTGGCCTC

ACTGATTATAAAAACACTTCTCAGGATTCTGGCGTACCGTTCCTGTCTA

AAATCCCTTTAATCGGCCTCCTGTTTAGCTCCCGCTCTGATTCTAACGA

GGAAAGCACGTTATACGTGCTCGTCAAAGCAACCATAGTACGCGCCCTG

TAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGG

GCTCCCTTTAGGGTTCCGATTTAGTGCTTTACGGCACCTCGACCCCAAA

AAACTTGATTAGGGTGATGGTTCACGTAGTGGGCCATCGCCCTGATAGA

CGGTTTTTCGCCCTTTGACGTTGGAGTCCACGTTCTTTAATAGTGGACT

CTTGTTCCAAACTGGAACAACACTCAACCCTATCTCGGTCTATTCTTTT

GATTTATAAGGGATTTTGCCGATTTCGGCCTATTGGTTAAAAAATGAGC

TGATTTAACAAAAATTTAACGCGAATTTTAACAAAATATTAACGTTTAC

AATTTAAATATTTGCTTATACAATCTTCCTGTTTTTGGGGCTTTTCTGA

TTATCAACCGGGGTACATATGATTGACATGCTAGTTTTACGATTACCGT

TCATCGATTCTCTTGTTTGCTCCAGACTCTCAGGCAATGACCTGATAGC

CTTTGTAGAGACCTCTCAAAAATAGCTACCCTCTCCGGCATGAATTTAT

CAGCTAGAACGGTTGAATATCATATTGATGGTGATTTGACTGTCTCCGG

CCTTTCTCACCCGTTTGAATCTTTACCTACACATTACTCAGGCATTGCA

TTTAAAATATATGAGGGTTCTAAAAATTTTTATCCTTGCGTTGAAATAA

AGGCTTCTCCCGCAAAAGTATTACAGGGTCATAATGTTTTTGGTACAAC

CGATTTAGCTTTATGCTCTGAGGCTTTATTGCTTAATTTTGCTAATTCT

TTGCCTTGCCTGTATGATTTATTGGATGTTGGAATTCCTGATGCGGTAT

TTTCTCCTTACGCATCTGTGCGGTATTTCACACCGCATATGGTGCACTC

TCAGTACAATCTGCTCTGATGCCGCATAGTTAAGCCAGCCCCGACACCC

GCCAACACCCGCTGACGCGCCCTGACGGGCTTGTCTGCTCCCGGCATCC

GCTTACAGACAAGCTGTGACCGTCTCCGGGAGCTGCATGTGTCAGAGGT

TTTCACCGTCATCACCGAAACGCGCGAGACGAAAGGGCCTCGTGATACG

CCTATTTTTATAGGTTAATGTCATGATAATAATGGTTTCTTAGACGTCA

GGTGGCACTTTTCGGGGAAATGTGCGCGGAACCCCTATTTGTTTATTTT

TCTAAATACATTCAAATATGTATCCGCTCATGAGACAATAACCCTGATA

AATGCTTCAATAATATTGAAAAAGGAAGAGTATGAGTATTCAACATTTC

CGTGTCGCCCTTATTCCCTTTTTTGCGGCATTTTGCCTTCCTGTTTTTG

CTCACCCAGAAACGCTGGTGAAAGTAAAAGATGCTGAAGATCAGTTGGG

TGCACGAGTGGGTTACATCGAACTGGATCTCAACAGCGGTAAGATCCTT

GAGAGTTTTCGCCCCGAAGAACGTTTTCCAATGATGAGCACTTTTAAAG

TTCTGCTATGTGGCGCGGTATTATCCCGTATTGACGCCGGGCAAGAGCA

ACTCGGTCGCCGCATACACTATTCTCAGAATGACTTGGTTGAGTACTCA

CCAGTCACAGAAAAGCATCTTACGGATGGCATGACAGTAAGAGAATTAT

GCAGTGCTGCCATAACCATGAGTGATAACACTGCGGCCAACTTACTTCT

GACAACGATCGGAGGACCGAAGGAGCTAACCGCTTTTTTGCACAACATG

GGGGATCATGTAACTCGCCTTGATCGTTGGGAACCGGAGCTGAATGAAG

CCATACCAAACGACGAGCGTGACACCACGATGCCTGTAGCAATGGCAAC

AACGTTGCGCAAACTATTAACTGGCGAACTACTTACTCTAGCTTCCCGG

CAACAATTAATAGACTGGATGGAGGCGGATAAAGTTGCAGGACCACTTC

TGCGCTCGGCCCTTCCGGCTGGCTGGTTTATTGCTGATAAATCTGGAGC

CGGTGAGCGTGGGTCTCGCGGTATCATTGCAGCACTGGGGCCAGATGGT

AAGCCCTCCCGTATCGTAGTTATCTACACGACGGGGAGTCAGGCAACTA

-continued

TGGATGAACGAAATAGACAGATCGCTGAGATAGGTGCCTCACTGATTAA

GCATTGGTAACTGTCAGACCAAGTTTACTCATATATACTTTAGATTGAT

TTAAAACTTCATTTTTAATTTAAAAGGATCTAGGTGAAGATCCTTTTTG

ATAATCTCATGACCAAAATCCCTTAACGTGAGTTTTCGTTCCACTGAGC

GTCAGACCCCGTAGAAAAGATCAAAGGATCTTCTTGAGATCCTTTTTTT

CTGCGCGTAATCTGCTGCTTGCAAACAAAAAAACCACCGCTACCAGCGG

TGGTTTGTTTGCCGGATCAAGAGCTACCAACTCTTTTTCCGAAGGTAAC

TGGCTTCAGCAGAGCGCAGATACCAAATACTGTCCTTCTAGTGTAGCCG

TAGTTAGGCCACCACTTCAAGAACTCTGTAGCACCGCCTACATACCTCG

CTCTGCTAATCCTGTTACCAGTGGCTGCTGCCAGTGGCGATAAGTCGTG

TCTTACCGGGTTGGACTCAAGACGATAGTTACCGGATAAGGCGCAGCGG

TCGGGCTGAACGGGGGGTTCGTGCACACAGCCCAGCTTGGAGCGAACGA

CCTACACCGAACTGAGATACCTACAGCGTGAGCTATGAGAAAGCGCCAC

GCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATC

TTTATAGTCCTGTCGGGTTTCGCCACCTCTGACTTGAGCGTCGATTTTT

GTGATGCTCGTCAGGGGGGCGGAGCCTATGGAAAAACGCCAGCAACGCG

GCCTTTTTACGGTTCCTGGCCTTTTGCTGGCCTTTTGCTCACATGTTCT

TTCCTGCGTTATCCCCTGATTCTGTGGATAACCGTATTACCGCCTTTGA

GTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCG

CGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGG

CCTCAGTGAGCGAGCGAGCGCGCAGAGAGGGAGTGGCCAACTCCATCAC

TAGGGGTTCCTTGTAGTTAATGATTAACCCGCCATGCTACTTATCTACG

TAGCCATGCTCTAGGACATTGATTATTGACTAGTGGAGTTCCGCGTTAC

ATAACTTACGGTAAATGGCCCGCCTGGCTGACCGCCCAACGACCCCCGC

CCATTGACGTCAATAATGACGTATGTTCCCATAGTAACGCCAATAGGGA

CTTTCCATTGACGTCAATGGGTGGAGTATTTACGGTAAACTGCCCACTT

GGCAGTACATCAAGTGTATCATATGCCAAGTACGCCCCCTATTGACGTC

AATGACGGTAAATGGCCCGCCTGGCATTATGCCCAGTACATGACCTTAT

GGGACTTTCCTACTTGGCAGTACATCTACGTATTAGTCATCGCTATTAC

CATGGTCGAGGTGAGCCCCACGTTCTGCTTCACTCTCCCCATCTCCCCC

CCCTCCCCACCCCCAATTTTGTATTTATTTATTTTTAATTATTTTGTG

CAGCGATGGGGCGGGGGGGGGGGGCGCGCGCCAGGCGGGGCGGGG

CGGGGCGAGGGCGGGCGGGGCGAGGCGGAGAGGTGCGGCGGCAGCCA

ATCAGAGCGGCGCGCTCCGAAAGTTTCCTTTTATGGCGAGGCGGCGGCG

GCGGCGGCCCTATAAAAAGCGAAGCGCGCGGCGGGGAGTCGCTGCG

CGCTGCCTTCGCCCCGTGCCCCGCTCCGCCGCCGCCTCGCGCCGCCCGC

CCCGGCTCTGACTGACCGCGTTACTAAAACAGGTAAGTCCGGCCTCCGC

GCCGGGTTTTGGCGCCTCCCGCGGGCGCCCCCCTCCTCACGGCGAGCGC

TGCCACGTCAGACGAAGGGCGCAGCGAGCGTCCTGATCCTTCCGCCCGG

ACGCTCAGGACAGCGGCCCGCTGCTCATAAGACTCGGCCTTAGAACCCC

AGTATCAGCAGAAGGACATTTTAGGACGGGACTTGGGTGACTCTAGGGC

ACTGGTTTTCTTTCCAGAGAGCGGAACAGGCGAGGAAAAGTAGTCCCTT

CTCGGCGATTCTGCGGAGGGATCTCCGTGGGGCGGTGAACGCCGATGAT

GCCTCTACTAACCATGTTCATGTTTTCTTTTTTTTTCTACAGGTCCTGG

GTGACGAACAGGGTACCGCCACCATGGCCACCGGCTCTCGCACAAGCCT

GCTGCTGGCTTTCGGACTGCTGTGCCTGCCTTGGCTCCAGGAGGGCTCC

GCCGCTAGCATCGATACCGTCGCTATGTGCTGGAGGCTTGCTGAAGGCT

GTATGCTGAGATAGTTGGTTGGGTGGTCTGCGTTTTGGCCTCTGACTGA

CGCAGACCACCACCAACTATCTCAGGACACAAGGCCTGTTACTAGCACT

CACATGGAACAAATGGCCTCTAGCCTGGAGGCTTGCTGAAGGCTGTATG

CTGTGCTAATCATCATACGGTCACGCGTTTTGGCCTCTGACTGACGCGT

GACCGTGATGATTAGCACAGGACACAAGGCCTGTTACTAGCACTCACAT

GGAACAAATGGCCTCTAGCCTGGAGGCTTGCTGAAGGCTGTATGCTGAC

ATAGCCCAGAACCAGGTAAACGTTTTGGCCTCTGACTGACGTTTACCTG

GCTGGGCTATGTCAGGACACAAGGCCTGTTACTAGCACTCACATGGAAC

AAATGGCCTCTCTAGAAT

3'

SEQ ID NO. 8 = SEQ ID NO. 1 + SEQ ID NO. 4
5'

AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTAAGCTTATCGATACCGTCGAGATCTAACTTGTTTATTGCAGCTTAT

AATGGTTACAAATAAAGCAATAGCATCACAAATTTCACAAATAAAGCAT

TTTTTTCACTGCATTCTAGTTGTGGTTTGTCCAAACTCATCAATGTATC

TTATCATGTCTGGATCTCGACCTCGACTAGAGCATGGCTACGTAGATAA

GTAGCATGGCGGGTTAATCATTAACTACAAGGAACCCCTAGTGATGGAG

TTGGCCACTCCCTCTCTGCGCGCTCGCTCGCTCACTGAGGCCGGGCGAC

-continued

CAAAGGTCGCCCGACGCCCGGGCTTTGCCCGGGCGGCCTCAGTGAGCGA

GCGAGCGCGCAGCTGGCGTAATAGCGAAGAGGCCCGCACCGATCGCCCT

TCCCAACAGTTGCGCAGCCTGAATGGCGAATGGCGATTCCGTTGCAATG

GCTGGCGGTAATATTGTTCTGGATATTACCAGCAAGGCCGATAGTTTGA

GTTCTTCTACTCAGGCAAGTGATGTTATTACTAATCAAAGAAGTATTGC

GACAACGGTTAATTTGCGTGATGGACAGACTCTTTTACTCGGTGGCCTC

ACTGATTATAAAAACACTTCTCAGGATTCTGGCGTACCGTTCCTGTCTA

AAATCCCTTTAATCGGCCTCCTGTTTAGCTCCCGCTCTGATTCTAACGA

GGAAAGCACGTTATACGTGCTCGTCAAAGCAACCATAGTACGCGCCCTG

TAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGG

GCTCCCTTTAGGGTTCCGATTTAGTGCTTTACGGCACCTCGACCCCAAA

AAACTTGATTAGGGTGATGGTTCACGTAGTGGGCCATCGCCCTGATAGA

CGGTTTTTCGCCCTTTGACGTTGGAGTCCACGTTCTTTAATAGTGGACT

CTTGTTCCAAACTGGAACAACACTCAACCCTATCTCGGTCTATTCTTTT

GATTTATAAGGGATTTTGCCGATTTCGGCCTATTGGTTAAAAAATGAGC

TGATTTAACAAAAATTTAACGCGAATTTTAACAAAATATTAACGTTTAC

AATTTAAATATTTGCTTATACAATCTTCCTGTTTTTGGGGCTTTTCTGA

TTATCAACCGGGGTACATATGATTGACATGCTAGTTTTACGATTACCGT

TCATCGATTCTCTTGTTTGCTCCAGACTCTCAGGCAATGACCTGATAGC

CTTTGTAGAGACCTCTCAAAAATAGCTACCCTCTCCGGCATGAATTTAT

CAGCTAGAACGGTTGAATATCATATTGATGGTGATTTGACTGTCTCCGG

CCTTTCTCACCCGTTTGAATCTTTACCTACACATTACTCAGGCATTGCA

TTTAAAATATATGAGGGTTCTAAAAATTTTTATCCTTGCGTTGAAATAA

AGGCTTCTCCCGCAAAAGTATTACAGGGTCATAATGTTTTTGGTACAAC

CGATTTAGCTTTATGCTCTGAGGCTTTATTGCTTAATTTTGCTAATTCT

TTGCCTTGCCTGTATGATTTATTGGATGTTGGAATTCCTGATGCGGTAT

TTTCTCCTTACGCATCTGTGCGGTATTTCACACCGCATATGGTGCACTC

TCAGTACAATCTGCTCTGATGCCGCATAGTTAAGCCAGCCCCGACACCC

GCCAACACCCGCTGACGCGCCCTGACGGGCTTGTCTGCTCCCGGCATCC

GCTTACAGACAAGCTGTGACCGTCTCCGGGAGCTGCATGTGTCAGAGGT

TTTCACCGTCATCACCGAAACGCGCGAGACGAAAGGGCCTCGTGATACG

CCTATTTTTATAGGTTAATGTCATGATAATAATGGTTTCTTAGACGTCA

GGTGGCACTTTTCGGGGAAATGTGCGCGGAACCCCTATTTGTTTATTTT

TCTAAATACATTCAAATATGTATCCGCTCATGAGACAATAACCCTGATA

AATGCTTCAATAATATTGAAAAAGGAAGAGTATGAGTATTCAACATTTC

CGTGTCGCCCTTATTCCCTTTTTTGCGGCATTTTGCCTTCCTGTTTTTG

CTCACCCAGAAACGCTGGTGAAAGTAAAAGATGCTGAAGATCAGTTGGG

TGCACGAGTGGGTTACATCGAACTGGATCTCAACAGCGGTAAGATCCTT

GAGAGTTTTCGCCCCGAAGAACGTTTTCCAATGATGAGCACTTTTAAAG

TTCTGCTATGTGGCGCGGTATTATCCCGTATTGACGCCGGGCAAGAGCA

ACTCGGTCGCCGCATACACTATTCTCAGAATGACTTGGTTGAGTACTCA

CCAGTCACAGAAAAGCATCTTACGGATGGCATGACAGTAAGAGAATTAT

GCAGTGCTGCCATAACCATGAGTGATAACACTGCGGCCAACTTACTTCT

GACAACGATCGGAGGACCGAAGGAGCTAACCGCTTTTTTGCACAACATG

GGGGATCATGTAACTCGCCTTGATCGTTGGGAACCGGAGCTGAATGAAG

CCATACCAAACGACGAGCGTGACACCACGATGCCTGTAGCAATGGCAAC

AACGTTGCGCAAACTATTAACTGGCGAACTACTTACTCTAGCTTCCCGG

CAACAATTAATAGACTGGATGGAGGCGGATAAAGTTGCAGGACCACTTC

TGCGCTCGGCCCTTCCGGCTGGCTGGTTTATTGCTGATAAATCTGGAGC

CGGTGAGCGTGGGTCTCGCGGTATCATTGCAGCACTGGGGCCAGATGGT

AAGCCCTCCCGTATCGTAGTTATCTACACGACGGGGAGTCAGGCAACTA

TGGATGAACGAAATAGACAGATCGCTGAGATAGGTGCCTCACTGATTAA

GCATTGGTAACTGTCAGACCAAGTTTACTCATATATACTTTAGATTGAT

TTAAAACTTCATTTTTAATTTAAAAGGATCTAGGTGAAGATCCTTTTTG

ATAATCTCATGACCAAAATCCCTTAACGTGAGTTTTCGTTCCACTGAGC

GTCAGACCCCGTAGAAAAGATCAAAGGATCTTCTTGAGATCCTTTTTTT

CTGCGCGTAATCTGCTGCTTGCAAACAAAAAAACCACCGCTACCAGCGG

TGGTTTGTTTGCCGGATCAAGAGCTACCAACTCTTTTTCCGAAGGTAAC

TGGCTTCAGCAGAGCGCAGATACCAAATACTGTCCTTCTAGTGTAGCCG

TAGTTAGGCCACCACTTCAAGAACTCTGTAGCACCGCCTACATACCTCG

CTCTGCTAATCCTGTTACCAGTGGCTGCTGCCAGTGGCGATAAGTCGTG

TCTTACCGGGTTGGACTCAAGACGATAGTTACCGGATAAGGCGCAGCGG

TCGGGCTGAACGGGGGGTTCGTGCACACAGCCCAGCTTGGAGCGAACGA

CCTACACCGAACTGAGATACCTACAGCGTGAGCTATGAGAAAGCGCCAC

GCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATC

TTTATAGTCCTGTCGGGTTTCGCCACCTCTGACTTGAGCGTCGATTTTT

GTGATGCTCGTCAGGGGGGCGGAGCCTATGGAAAAACGCCAGCAACGCG

GCCTTTTTACGGTTCCTGGCCTTTTGCTGGCCTTTTGCTCACATGTTCT

TTCCTGCGTTATCCCCTGATTCTGTGGATAACCGTATTACCGCCTTTGA

GTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCG

CGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGG

CCTCAGTGAGCGAGCGAGCGCGCAGAGAGGGAGTGGCCAACTCCATCAC

TAGGGGTTCCTTGTAGTTAATGATTAACCCGCCATGCTACTTATCTACG

TAGCCATGCTCTAGGACATTGATTATTGACTAGTGGAGTTCCGCGTTAC

ATAACTTACGGTAAATGGCCCGCCTGGCTGACCGCCCAACGACCCCCGC

CCATTGACGTCAATAATGACGTATGTTCCCATAGTAACGCCAATAGGGA

21

-continued

CTTTCCATTGACGTCAATGGGTGGAGTATTTACGGTAAACTGCCCACTT

GGCAGTACATCAAGTGTATCATATGCCAAGTACGCCCCCTATTGACGTC

AATGACGGTAAATGGCCCGCCTGGCATTATGCCCAGTACATGACCTTAT

GGGACTTTCCTACTTGGCAGTACATCTACGTATTAGTCATCGCTATTAC

CATGGTCGAGGTGAGCCCCACGTTCTGCTTCACTCTCCCCATCTCCCCC

CCCTCCCCACCCCCAATTTTGTATTTATTTATTTTTTAATTATTTTGTG

CAGCGATGGGGCGGGGGGGGGGGGGCGCGCGCCAGGCGGGGGGGG

GGGGCGAGGGGCGGGGCGGGGCGAGGCGGAGAGGTGCGGCGGCAGCCAA

TCAGAGCGGCGCGCTCCGAAAGTTTCCTTTTATGGCGAGGCGGCGGCGG

CGGCGGCCCTATAAAAAGCGAAGCGCGCGGCGGGCGGGAGTCGCTGCGC

GCTGCCTTCGCCCCGTGCCCCGCTCCGCCGCCGCCTCGCGCCGCCCGCC

CCGGCTCTGACTGACCGCGTTACTAAAACAGGTAAGTCCGGCCTCCGCG

CCGGGTTTTGGCGCCTCCCGCGGGCGCCCCCCTCCTCACGGCGAGCGCT

GCCACGTCAGACGAAGGGCGCAGCGAGCGTCCTGATCCTTCCGCCCGGA

CGCTCAGGACAGCGGCCCGCTGCTCATAAGACTCGGCCTTAGAACCCCA

GTATCAGCAGAAGGACATTTTAGGACGGGACTTGGGTGACTCTAGGGCA

CTGGTTTTCTTTCCAGAGAGCGGAACAGGCGAGGAAAAGTAGTCCCTTC

TCGGCGATTCTGCGGAGGGATCTCCGTGGGCGGTGAACGCCGATGATG

CCTCTACTAACCATGTTCATGTTTTCTTTTTTTTCTACAGGTCCTGGG

TGACGAACAGGGTACCGCCACCATGGCCACCGGCTCTCGCACAAGCCTG

CTGCTGGCTTTCGGACTGCTGTGCCTGCCTTGGCTCCAGGAGGGCTCCG

CCGCTAGCATCGATACCGTCGCTATGTGCTGGAGGCTTGCTGAAGGCT

TATGCTGAGATAGTTGGTTGGGTGGTCTGCGTTTTGGCCTCTGACTGAC

GCAGACCACCACCAACTATCTCAGGACACAAGGCCTGTTACTAGCACTC

ACATGGAACAAATGGCCTCTAGCCTGGAGGCTTGCTGAAGGCTGTATGC

TGTTTCTTCGCGTTGTTCAGTTCGCGTTTTGGCCTCTGACTGACGCGAA

CTGAAACGCGAAGAAACAGGACACAAGGCCTGTTACTAGCACTCACATG

GAACAAATGGCCTCTAGCCTGGAGGCTTGCTGAAGGCTGTATGCTGTTT

CTTCGCGTAATTCAGTTCGCGTTTTGGCCTCTGACTGACGCGAACTGAA

ACGCGAAGAAACAGGACACAAGGCCTGTTACTAGCACTCACATGAACA

AATGGCCTCTCTAGAAT

3'

SEQ ID NO. 9 = SEQ ID NO. 1 + SEQ ID NO. 5
5'

AATCAACCTCTGGATTACAAAATTTGTGAAAGATTGACTGGTATTCTTA

ACTATGTTGCTCCTTTTACGCTATGTGGATACGCTGCTTTAATGCCTTT

GTATCATGCTATTGCTTCCCGTATGGCTTTCATTTTCTCCTCCTTGTAT

AAATCCTGGTTGCTGTCTCTTTATGAGGAGTTGTGGCCCGTTGTCAGGC

AACGTGGCGTGGTGTGCACTGTGTTTGCTGACGCAACCCCCACTGGTTG

22

-continued

GGGCATTGCCACCACCTGTCAGCTCCTTTCCGGGACTTTCGCTTTCCCC

CTCCCTATTGCCACGGCGGAACTCATCGCCGCCTGCCTTGCCCGCTGCT

GGACAGGGGCTCGGCTGTTGGGCACTGACAATTCCGTGGTGTTGTCGGG

GAAATCATCGTCCTTTCCTTGGCTGCTCGCCTGTGTTGCCACCTGGATT

CTGCGCGGGACGTCCTTCTGCTACGTCCCTTCGGCCCTCAATCCAGCGG

ACCTTCCTTCCCGCGGCCTGCTGCCGGCTCTGCGGCCTCTTCCGCGTCT

TCGCCTTCGCCCTCAGACGAGTCGGATCTCCCTTTGGGCCGCCTCCCCG

CCTAAGCTTATCGATACCGTCGAGATCTAACTTGTTTATTGCAGCTTAT

AATGGTTACAAATAAAGCAATAGCATCACAAATTTCACAAATAAAGCAT

TTTTTTCACTGCATTCTAGTTGTGGTTTGTCCAAACTCATCAATGTATC

TTATCATGTCTGGATCTCGACCTCGACTAGAGCATGGCTACGTAGATAA

GTAGCATGGCGGGTTAATCATTAACTACAAGGAACCCCTAGTGATGGAG

TTGGCCACTCCCTCTCTGCGCGCTCGCTCGCTCACTGAGGCCGGGCGAC

CAAAGGTCGCCCGACGCCCGGGCTTTGCCCGGGCGGCCTCAGTGAGCGA

GCGAGCGCGCAGCTGGCGTAATAGCGAAGAGGCCCGCACCGATCGCCCT

TCCCAACAGTTGCGCAGCCTGAATGGCGAATGGCGATTCCGTTGCAATG

GCTGGCGGTAATATTGTTCTGGATATTACCAGCAAGGCCGATAGTTTGA

GTTCTTCTACTCAGGCAAGTGATGTTATTACTAATCAAAGAAGTATTGC

GACAACGGTTAATTTGCGTGATGGACAGACTCTTTTACTCGGTGGCCTC

ACTGATTATAAAAACACTTCTCAGGATTCTGGCGTACCGTTCCTGTCTA

AAATCCCTTTAATCGGCCTCCTGTTTAGCTCCCGCTCTGATTCTAACGA

GGAAAGCACGTTATACGTGCTCGTCAAAGCAACCATAGTACGCGCCCTG

TAGCGGCGCATTAAGCGCGGCGGGTGTGGTGGTTACGCGCAGCGTGACC

GCTACACTTGCCAGCGCCCTAGCGCCCGCTCCTTTCGCTTTCTTCCCTT

CCTTTCTCGCCACGTTCGCCGGCTTTCCCCGTCAAGCTCTAAATCGGGG

GCTCCCTTTAGGGTTCCGATTTAGTGCTTTACGGCACCTCGACCCCAAA

AAACTTGATTAGGGTGATGGTTCACGTAGTGGGCCATCGCCCTGATAGA

CGGTTTTTCGCCCTTTGACGTTGGAGTCCACGTTCTTTAATAGTGGACT

CTTGTTCCAAACTGGAACAACACTCAACCCTATCTCGGTCTATTCTTTT

GATTTATAAGGGATTTTGCCGATTTCGGCCTATTGGTTAAAAAATGAGC

TGATTTAACAAAAATTTAACGCGAATTTTAACAAAATATTAACGTTTAC

AATTTAAATATTTGCTTATACAATCTTCCTGTTTTTGGGGCTTTTCTGA

TTATCAACCGGGGTACATATGATTGACATGCTAGTTTTACGATTACCGT

TCATCGATTCTCTTGTTTGCTCCAGACTCTCAGGCAATGACCTGATAGC

CTTTGTAGAGACCTCTCAAAAATAGCTACCCTCTCCGGCATGAATTTAT

CAGCTAGAACGGTTGAATATCATATTGATGGTGATTTGACTGTCTCCGG

CCTTTCTCACCCGTTTGAATCTTTACCTACACATTACTCAGGCATTGCA

TTTAAAATATATGAGGGTTCTAAAATTTTTATCCTTGCGTTGAAATAA

AGGCTTCTCCCGCAAAAGTATTACAGGGTCATAATGTTTTTGGTACAAC

CGATTTAGCTTTATGCTCTGAGGCTTTATTGCTTAATTTTGCTAATTCT

TTGCCTTGCCTGTATGATTTATTGGATGTTGGAATTCCTGATGCGGTAT

-continued

TTTCTCCTTACGCATCTGTGCGGTATTTCACACCGCATATGGTGCACTC

TCAGTACAATCTGCTCTGATGCCGCATAGTTAAGCCAGCCCCGACACCC

GCCAACACCCGCTGACGCGCCCTGACGGGCTTGTCTGCTCCCGGCATCC

GCTTACAGACAAGCTGTGACCGTCTCCGGGAGCTGCATGTGTCAGAGGT

TTTCACCGTCATCACCGAAACGCGCGAGACGAAAGGGCCTCGTGATACG

CCTATTTTTATAGGTTAATGTCATGATAATAATGGTTTCTTAGACGTCA

GGTGGCACTTTTCGGGGAAATGTGCGCGGAACCCCTATTTGTTTATTTT

TCTAAATACATTCAAATATGTATCCGCTCATGAGACAATAACCCTGATA

AATGCTTCAATAATATTGAAAAGGAAGAGTATGAGTATTCAACATTTC

CGTGTCGCCCTTATTCCCTTTTTTGCGGCATTTTGCCTTCCTGTTTTTG

CTCACCCAGAAACGCTGGTGAAAGTAAAAGATGCTGAAGATCAGTTGGG

TGCACGAGTGGGTTACATCGAACTGGATCTCAACAGCGGTAAGATCCTT

GAGAGTTTTCGCCCCGAAGAACGTTTTCCAATGATGAGCACTTTTAAAG

TTCTGCTATGTGGCGCGGTATTATCCCGTATTGACGCCGGGCAAGAGCA

ACTCGGTCGCCGCATACACTATTCTCAGAATGACTTGGTTGAGTACTCA

CCAGTCACAGAAAAGCATCTTACGGATGGCATGACAGTAAGAGAATTAT

GCAGTGCTGCCATAACCATGAGTGATAACACTGCGGCCAACTTACTTCT

GACAACGATCGGAGGACCGAAGGAGCTAACCGCTTTTTTGCACAACATG

GGGGATCATGTAACTCGCCTTGATCGTTGGGAACCGGAGCTGAATGAAG

CCATACCAAACGACGAGCGTGACACCACGATGCCTGTAGCAATGGCAAC

AACGTTGCGCAAACTATTAACTGGCGAACTACTTACTCTAGCTTCCCGG

CAACAATTAATAGACTGGATGGAGGCGGATAAAGTTGCAGGACCACTTC

TGCGCTCGGCCCTTCCGGCTGGCTGGTTTATTGCTGATAAATCTGGAGC

CGGTGAGCGTGGGTCTCGCGGTATCATTGCAGCACTGGGGCCAGATGGT

AAGCCCTCCCGTATCGTAGTTATCTACACGACGGGGAGTCAGGCAACTA

TGGATGAACGAAATAGACAGATCGCTGAGATAGGTGCCTCACTGATTAA

GCATTGGTAACTGTCAGACCAAGTTTACTCATATATACTTTAGATTGAT

TTAAAACTTCATTTTTAATTTAAAAGGATCTAGGTGAAGATCCTTTTTG

ATAATCTCATGACCAAAATCCCTTAACGTGAGTTTTCGTTCCACTGAGC

GTCAGACCCCGTAGAAAAGATCAAAGGATCTTCTTGAGATCCTTTTTTT

CTGCGCGTAATCTGCTGCTTGCAAACAAAAAAACCACCGCTACCAGCGG

TGGTTTGTTTGCCGGATCAAGAGCTACCAACTCTTTTTCCGAAGGTAAC

TGGCTTCAGCAGAGCGCAGATACCAAATACTGTCCTTCTAGTGTAGCCG

TAGTTAGGCCACCACTTCAAGAACTCTGTAGCACCGCCTACATACCTCG

CTCTGCTAATCCTGTTACCAGTGGCTGCTGCCAGTGGCGATAAGTCGTG

TCTTACCGGGTTGGACTCAAGACGATAGTTACCGGATAAGGCGCAGCGG

TCGGGCTGAACGGGGGGTTCGTGCACACAGCCCAGCTTGGAGCGAACGA

CCTACACCGAACTGAGATACCTACAGCGTGAGCTATGAGAAAGCGCCAC

GCTTCCCGAAGGGAGAAAGGCGGACAGGTATCCGGTAAGCGGCAGGGTC

GGAACAGGAGAGCGCACGAGGGAGCTTCCAGGGGGAAACGCCTGGTATC

-continued

TTTATAGTCCTGTCGGGTTTCGCCACCTCTGACTTGAGCGTCGATTTTT

GTGATGCTCGTCAGGGGGCGGAGCCTATGGAAAAACGCCAGCAACGCG

GCCTTTTTACGGTTCCTGGCCTTTTGCTGGCCTTTTGCTCACATGTTCT

TTCCTGCGTTATCCCCTGATTCTGTGGATAACCGTATTACCGCCTTTGA

GTGAGCTGATACCGCTCGCCGCAGCCGAACGACCGAGCGCAGCGAGTCA

GTGAGCGAGGAAGCGGAAGAGCGCCCAATACGCAAACCGCCTCTCCCCG

CGCGTTGGCCGATTCATTAATGCAGCAGCTGCGCGCTCGCTCGCTCACT

GAGGCCGCCCGGGCAAAGCCCGGGCGTCGGGCGACCTTTGGTCGCCCGG

CCTCAGTGAGCGAGCGAGCGCGCAGAGAGGGAGTGGCCAACTCCATCAC

TAGGGGTTCCTTGTAGTTAATGATTAACCCGCCATGCTACTTATCTACG

TAGCCATGCTCTAGGACATTGATTATTGACTAGTGGAGTTCCGCGTTAC

ATAACTTACGGTAAATGGCCCGCCTGGCTGACCGCCCAACGACCCCCGC

CCATTGACGTCAATAATGACGTATGTTCCCATAGTAACGCCAATAGGGA

CTTTCCATTGACGTCAATGGGTGGAGTATTTACGGTAAACTGCCCACTT

GGCAGTACATCAAGTGTATCATATGCCAAGTACGCCCCCTATTGACGTC

AATGACGGTAAATGGCCCGCCTGGCATTATGCCCAGTACATGACCTTAT

GGGACTTTCCTACTTGGCAGTACATCTACGTATTAGTCATCGCTATTAC

CATGGTCGAGGTGAGCCCCACGTTCTGCTTCACTCTCCCCATCTCCCCC

CCCTCCCCACCCCCAATTTTGTATTTATTTATTTTTTAATTATTTTGTG

CAGCGATGGGGGCGGGGGGGGGGGGGCGCGCGCCAGGCGGGGCGGGG

GGGGGCGAGGGGGGGCGGGGCGAGGCGGAGAGGTGCGGCGGCAGCCAA

TCAGAGCGGCGCGCTCCGAAAGTTTCCTTTTATGGCGAGGCGGCGGCGG

CGGCGGCCCTATAAAAAGCGAAGCGCGCGGCGGGCGGGAGTCGCTGCGC

GCTGCCTTCGCCCCGTGCCCCGCTCCGCCGCCGCCTCGCGCCGCCCGCC

CCGGCTCTGACTGACCGCGTTACTAAAACAGGTAAGTCCGGCCTCCGCG

CCGGGTTTTGGCGCCTCCCGCGGGCGCCCCCCTCCTCACGGCGAGCGCT

GCCACGTCAGACGAAGGGCGCAGCGAGCGTCCTGATCCTTCCGCCCGGA

CGCTCAGGACAGCGGCCCGCTGCTCATAAGACTCGGCCTTAGAACCCCA

GTATCAGCAGAAGGACATTTTAGGACGGGACTTGGGTGACTCTAGGGCA

CTGGTTTTCTTTCCAGAGAGCGGAACAGGCGAGGAAAAGTAGTCCCTTC

TCGGCGATTCTGCGGAGGGATCTCCGTGGGCGGTAACGCCGATGATG

CCTCTACTAACCATGTTCATGTTTTCTTTTTTTTCTACAGGTCCTGGG

TGACGAACAGGGTACCGCCACCATGGCCACCGGCTCTCGCACAAGCCTG

CTGCTGGCTTTCGGACTGCTGTGCCTGCCTTGGCTCCAGGAGGGCTCCG

CCGCTAGCATCGATACCGTCGCTATGTGCTGGAGGCTTGCTGAAGGCTG

TATGCTGATAAATCACCGTGGGTTCAGCGCGTTTTGGCCTCTGACTGAC

GCGCTGAACCCGGTGATTTATCAGGACAAGGCCTGTTACTAGCACTC

ACATGGAACAAATGGCCTCTAGCCTGGAGGCTTGCTGAAGGCTGTATGC

TGATAAATCACCGATGGTTCAGCGCGTTTTGGCCTCTGACTGACGCGCT

GAACCCGGTGATTTATCAGGACACAAGGCCTGTTACTAGCACTCACATG

GAACAAATGGCCTCTAGCCTGGAGGCTTGCTGAAGGCTGTATGCTGATA

-continued

```
AATCACCGAAGGTTCAGCGCGTTTTGGCCTCTGACTGACGCGCTGAACC

CGGTGATTTATCAGGACACAAGGCCTGTTACTAGCACTCACATGGAACA

AATGGCCTCTCTAGAAT
```

3'

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 6. SEQ ID NO. 7. SEQ ID NO. 8 or SEQ ID NO. 9, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes were integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) with a sequence of nucleotides that comprise a start region, an end region and an insert positioned between the start region and the end region, in which the insert encodes for a sequence of micro-interfering ribonucleic acid (miRNA) that binds to and causes degradation of messenger ribonucleic acid (mRNA) that encodes for a dopamine receptor, wherein the insert sequence comprises 95-100% of the same nucleotide sequence as one of SEQ ID NO. 2, SEQ ID NO. 3, SEQ ID NO. 4 or SEQ ID NO. 5.

2. The composition of claim 1, wherein the sequence of nucleotides is configured to be delivered to a target cell that has an over-expressed or mis-expressed biomolecule, wherein the sequence of nucleotides is encased in a protein coat, a lipid vesicle, or any combination thereof.

3. The composition of claim 1, wherein the sequence of nucleotides is configured to be delivered to a target cell that has an over-expressed or mis-expressed biomolecule, wherein the sequence of nucleotides is encased in a viral vector.

4. The composition of claim 3, wherein the virus viral vector is a double stranded DNA virus, a single stranded DNA virus, a single stranded RNA virus, or a double stranded RNA virus.

5. The composition of claim 4, wherein the viral vector is an adeno-associated virus.

6. The composition of claim 1 wherein the dopamine receptor is one of the D1 dopamine receptor, the D2 dopamine receptor, the D3 dopamine receptor, or the D4 dopamine receptor.

7. The composition of claim 1, wherein the insert sequence comprises 95-100% of the same nucleotide sequence as SEQ ID NO. 2.

8. The composition of claim 1, wherein the insert sequence comprises 95-100% of the same nucleotide sequence as SEQ ID NO. 3.

9. The composition of claim 1, wherein the insert sequence comprises 95-100% of the same nucleotide sequence as SEQ ID NO. 4.

10. The composition of claim 1, wherein the insert comprises 95-100% of the same nucleotide sequence as SEQ ID NO. 5.

11. A composition that comprises a recombinant plasmid (RP) with a sequence of nucleotides that encodes for a sequence of micro-interfering ribonucleic acid (miRNA) that binds to and causes degradation of messenger ribonucleic acid (mRNA) that encodes for a dopamine receptor, wherein the sequence is one of SEQ ID NO. 6, SEQ ID NO. 7, SEQ ID NO. 8, or SEQ ID NO. 9.

12. The composition of claim 11, wherein the sequence is SEQ ID NO. 6.

13. The composition of claim 11, wherein the sequence is SEQ ID NO. 7.

14. The composition of claim 11, wherein the sequence is SEQ ID NO. 8.

15. The composition of claim 11, wherein the sequence is SEQ ID NO. 9.

* * * * *

SEQUENCE LISTING

```
Sequence total quantity: 9
SEQ ID NO: 1           moltype = DNA   length = 5799
FEATURE                Location/Qualifiers
source                 1..5799
                       mol_type = other DNA
                       organism = synthetic construct
SEQUENCE: 1
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccccctcct  300
attgccacgc cggaactcat cgccgcctgc cttgcccgct gctggacagg ggctcggctg  360
ttgggcactg acaattccgt ggtgttgtcg gggaaatcat cgtccttttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctcccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcgcg gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg ctcccctta gggttccgat ttagtgcttt 1500
acggcacctc gaccccaaaa aacttgatta gggtgatggt tcacgtagtg ggccatcgcc 1560
ctgatagacg gttttttcgcc ctttgacgtt ggagtccacg ttctttaata gtggactctt 1620
gttccaaact ggaacaacac tcaacctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
```

-continued

```
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgttttggg tacaaccgat  2160
ttagctttat gctctgaggc tttattgctt aattttgcta attctttgcc ttgcctgtat  2220
gatttattgg atgttggaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaagggcct cgtgatacgc ctattttat aggttaatgt  2520
catgataata atggtttctt agacgtcagg tggcactttt cggggaaatg tgcgcggaac  2580
ccctatttgt ttattttct aaatacattc aaatatgtat ccgctcatga gacaataacc  2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgag  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatggca tgacagtaag agaattatgc agtgctgcca taaccatgag  3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatggaggcg gataaagttg caggaccact tctgcgctcg gcccttccgg ctggctggtt  3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcagaccaa gtttactcat atatacttta gattgattta aaacttcatt tttaatttaa  3600
aaggatctag gtgaagatcc tttttgataa tctcatgacc aaaatccctt aacgtgagtt  3660
ttcgttccac tgagcgtcag accccgtaga aagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtccttc tagtgtagcc gtagttaggc caccacttca agaactctgt  3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg ggggggtcgt gcacacagcc cagcttggag gaacgaccta cacccgaact  4080
gagataccta cagcgtgagc tatgagaaag cgccacgctt cccgaaggga gaaaggcgga  4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg gcggagcct atggaaaaac gccagcaacg cggcctttt  4320
acggttcctg gccttttgct ggccttttgc tcacatgttc tttcctgcgt tatccctga  4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagggagt ggccaactcc atcactaggg gttccttgta gttaatgatt  4680
aacccgccat gctacttatc tacgtagcca tgctctagga cattgattat tgactagtgg  4740
agttccgcgt tacataactt acggtaaatg gcccgcctgg ctgaccgccc aacgacccc  4800
gcccattgac gtcaataatg acgtatgttc ccatagtaac gccaataggg acttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tccccccct tccccccct  5100
ccccacccc aattttgtat ttatttattt ttaattatt ttgtgcagcg atggggcgg  5160
gggggggggg gggcgcgcgc caggcggggc ggggcgggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccgctcgc  5400
actgaccgcg ttactaaaac aggtaagtcc ggcctccgcg ccgggtttt gcgcctcccg  5460
cgggcgcccc cctcctcacg gcgagcgctg ccacgtcaga cgaagggcgc agcgagcgtc  5520
ctgatcctcc cgcccggacg ctcaggacag cggcccgctg ctcataagac tcggcctag  5580
aaccccagta tcagcagaag gacatttag gacgggactt gggtgactct agggcactgg  5640
tttctcttcc agagagcgga acaggcgagg aaaagtagtc ccttctcggc gattctgcgg  5700
agggatctcc gtggggcggt gaacgccgat gatgcctcta ctaaccatgt tcatgttttc  5760
tttttttc tacaggtcct gggtgacgaa cagggtacc                          5799
```

```
SEQ ID NO: 2           moltype = DNA   length = 540
FEATURE                Location/Qualifiers
source                 1..540
                       mol_type = other DNA
                       organism = synthetic construct
SEQUENCE: 2
gccaccatgg ccaccggctc tcgcacaagc ctgctgctgg ctttcggact gctgtgcctg  60
ccttggctcc aggagggctc cgccgctagc atcgataccg tcgctatgtg ctgaggctt  120
gctgaaggct gtatgctgta tcaatggttt gtccgccagg cgttttggcc tctgactgac  180
gcctggcgga aaccattgat acaggacaca aggcctgtta ctagcactca catgaacaa  240
atggcctcta gcctggaggc ttgctgaagg ctgtatgctg aaataatcgg gatttcaggc  300
tgcgttttgg cctctgactg acgcagcctg aacccgatta tttcaggaca caaggcctgt  360
tactagcact cacatggaac aaatggcctc tagcctggag gcttgctgaa ggctgtatgc  420
```

```
tgattctttg ctaaaatgct gccgcgtttt ggcctctgac tgacgcggca gcattagcaa    480
agaatcagga cacaaggcct gttactagca ctcacatgga acaaatggcc tctctagaat    540
```

| SEQ ID NO: 3 | moltype = DNA   length = 540 |
|---|---|
| FEATURE | Location/Qualifiers |
| source | 1..540 |
|  | mol_type = other DNA |
|  | organism = synthetic construct |

SEQUENCE: 3
```
gccaccatgg ccaccggctc tcgcacaagc ctgctgctgg ctttcggact gctgtgcctg     60
ccttggctcc aggagggctc cgccgctagc atcgataccg tcgctatgtg ctggaggctt    120
gctgaaggct gtatgctgag atagttggtt gggtggtctg cgttttggcc tctgactgac    180
gcagaccacc accaactatc tcaggacaca aggcctgtta ctagcactca catggaacaa    240
atggcctcta gcctggaggc ttgctgaagg ctgtatgctg tgctaatcat catacggtca    300
cgcgttttgg cctctgactg acgcgtgacc gtgatgatta gcacaggaca caaggcctg    360
tactagcact cacatggaac aaatggcctc tagcctggag gcttgctgaa ggctgtatgc    420
tgacatagcc agaaccagg taaacgtttt ggcctctgac tgacgtttac ctggctgggc    480
tatgtcagga cacaaggcct gttactagca ctcacatgga acaaatggcc tctctagaat    540
```

| SEQ ID NO: 4 | moltype = DNA   length = 540 |
|---|---|
| FEATURE | Location/Qualifiers |
| source | 1..540 |
|  | mol_type = other DNA |
|  | organism = synthetic construct |

SEQUENCE: 4
```
gccaccatgg ccaccggctc tcgcacaagc ctgctgctgg ctttcggact gctgtgcctg     60
ccttggctcc aggagggctc cgccgctagc atcgataccg tcgctatgtg ctggaggctt    120
gctgaaggct gtatgctgag atagttggtt gggtggtctg cgttttggcc tctgactgac    180
gcagaccacc accaactatc tcaggacaca aggcctgtta ctagcactca catggaacaa    240
atggcctcta gcctggaggc ttgctgaagg ctgtatgctg tttcttccg ttgttcagtt    300
cgcgttttgg cctctgactg acgcgaactg aaacgcgaag aaacaggaca caaggcctg    360
tactagcact cacatggaac aaatggcctc tagcctggag gcttgctgaa ggctgtatgc    420
tgtttcttcg cgtaattcag ttcgcgtttt ggcctctgac tgacgcgaac tgaaacgcga    480
agaaacagga cacaaggcct gttactagca ctcacatgga acaaatggcc tctctagaat    540
```

| SEQ ID NO: 5 | moltype = DNA   length = 540 |
|---|---|
| FEATURE | Location/Qualifiers |
| source | 1..540 |
|  | mol_type = other DNA |
|  | organism = synthetic construct |

SEQUENCE: 5
```
gccaccatgg ccaccggctc tcgcacaagc ctgctgctgg ctttcggact gctgtgcctg     60
ccttggctcc aggagggctc cgccgctagc atcgataccg tcgctatgtg ctggaggctt    120
gctgaaggct gtatgctgat aaatcaccgt gggttcagcg cgttttggcc tctgactgac    180
gcgctgaacc cggtgattta tcaggacaca aggcctgtta ctagcactca catggaacaa    240
atggcctcta gcctggaggc ttgctgaagg ctgtatgctg ataaatcacc gatggttcag    300
cgcgttttgg cctctgactg acgcgctgaa cccggtgattt atcaggaca caaggcctg    360
tactagcact cacatggaac aaatggcctc tagcctggag gcttgctgaa ggctgtatgc    420
tgataaatca ccgaaggttc agcgcgtttt ggcctctgac tgacgcgctg aacccggtga    480
tttatcagga cacaaggcct gttactagca ctcacatgga acaaatggcc tctctagaat    540
```

| SEQ ID NO: 6 | moltype = DNA   length = 6339 |
|---|---|
| FEATURE | Location/Qualifiers |
| source | 1..6339 |
|  | mol_type = other DNA |
|  | organism = synthetic construct |

SEQUENCE: 6
```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240
ggttgggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtca gatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgactcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacgttaat   1140
ttgcgtgatg gacagactct tttactcggt ggcctcactg attataaaaa cacttctcag   1200
gattctggcg taccgttcct gtctaaaatc ccttttaatcg gcctcctgtt tagctcccgc   1260
tctgattcta acgaggaaag cacgttatac gtgctcgtca aagcaaccat agtacgcgcc   1320
```

```
ctgtagcggc gcattaagcg cggcgggtgt ggtggttacg cgcagcgtga ccgctacact   1380
tgccagcgcc ctagcgcccg ctcctttcgc tttcttccct tccttttctcg ccacgttcgc   1440
cggctttccc cgtcaagctc taaatcgggg gctccctttta gggttccgat ttagtgcttt   1500
acggcacctc gaccccaaaa aacttgatta gggtgatggt tcacgtagtg ggccatcgcc   1560
ctgatagacg gttttttcgcc cttttgacgtt ggagtccacg ttctttaata gtggactctt   1620
gttccaaact ggaacaacac tcaacccta ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgg ccctgacggg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acgatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acgggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaaacgcctgg tatctttata gtcctgtcgg gtttcgccac ctctgacttg agcgtcgatt   4260
tttgtgatgc tcgtcagggg gcggagcct atggaaaaac gccagcaacg cggccttttt   4320
acggttcgtg gcctttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctactatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
cccacccccc aattttgtat ttatttattt tttaattatt ttgtgcagcg atgggggcgg   5160
gggggggggg gggcgcgcgc caggcggggc ggggcgggggc gagggcgggg cggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggcgccctc   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aacccccagta tcagcagaag gacatttag gacgggactt gggtgactct agggcactgg   5640
ttttcttttcc agagagcgga acaggcgagg aaaagtagtc ccttctcggc gattctgcgg   5700
agggatcgcc gtggggcggt gaacgccgat gatgcctcta ctaaccatgt tcatgtttcc   5760
ttttttttttc tacaggtcct gggtgacgaa caggtaccg ccaccatggc caccggctct   5820
cgcacaagcc tgctgctggc tttcggactc tgtgcctgc cttggctcca ggagggctcc   5880
gccgctagca tcgataccgt cgctatgtgc tggaggcttg ctgaaggctg tatgctgtat   5940
caatggtttg tccgccaggc gttttggcct ctgactgacg cctggcggaa accattgata   6000
cagggacacaa ggcctgttac tagcactcac atggaacaaa tggcctctag cctggaggct   6060
```

```
tgctgaaggc tgtatgctga aataatcggg atttcaggct gcgttttggc ctctgactga    6120
cgcagcctga acccgattat ttcaggacac aaggcctgtt actagcactc acatggaaca    6180
aatggcctct agcctggagg cttgctgaag gctgtatgct gattcttgc taaaatgctg     6240
ccgcgttttg gcctctgact gacgcggcag cattagcaaa gaatcaggac acaaggcctg    6300
ttactagcac tcacatggaa caaatggcct ctctagaat                           6339
```

```
SEQ ID NO: 7              moltype = DNA   length = 6339
FEATURE                   Location/Qualifiers
source                    1..6339
                          mol_type = other DNA
                          organism = synthetic construct
SEQUENCE: 7
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact   240
ggttggggca ttgccaccac ctgtcagctc ctttccggga ctttcgcttt cccctcct     300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttcctc ccgcggcctg ctgccggctc tgcggcctct tccgcgtctt     540
cgccttcgcc ctcagacgag tcggatctcc ctttgggcg cctccccgcc taagcttaaa     600
gataccgtcg agatctaact tgtttattgc agcttataat ggttacaaat aaagcaatag    660
catcacaaat ttcacaaata aagcatttt ttcactgcat tctagttgtg gtttgtccaa     720
actcatcaat gtatcttatc atgtctggat ctcgacctcg actagagcat ggctacgtag    780
ataagtagca tggcgggtta atcattaact acaaggaacc ctagtagtg gagttggcca    840
ctccctctct gcgcgctcgc tcgctcactg aggccgggcg accaaaggtc gcccgacgcg    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttta gggttccgat ttagtgcttt    1500
acggcacctc gaccccaaaa aacttgatta gggtgatggt tcacgtagtg gccatcgcc    1560
ctgatagacg gttttcgcc ctttgacgtt ggagtccacg ttctttaata gtggactctt    1620
gttccaaact ggaacaacac tcaacccat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaaatatat gagggttcta aaaattttta tccttgcgtt    2100
gaaataaagg cttctcccgc aaaagtatta caggggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacacgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcacttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acgatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt    3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttgataa tctcatgacc aaaatccctt aacgtgagtt    3660
ttcgttccac tgagcgtcag accccgtaga aagatcaaa ggatcttctt gagatccttt   3720
ttttctgcgc gtaatctgct gcttgcaaac aaaaaaacca ccgctaccag cggtggtttg   3780
tttgccggat caagagctac caactcttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
```

```
gggctgaacg gggggttcgt gcacacagcc cagcttggag cgaacgacct acaccgaact    4080
gagataccta cagcgtgagc tatgagaaag cgccacgctt cccgaaggga gaaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggccttttt    4320
acggttcctg gccttttgct ggccttttgc tcacatgttc tttcctgcgt tatccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgaccccc    4800
gcccattgac gtcaataatg acgtatgttc ccatagtaac gccaataggg acttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
ccccacccc aattttgtat ttatttattt tttaattatt ttgtgcagcg atggggggcgg    5160
gggggggggg gggcgcgcgc caggcggggc ggggcggggc gaggggcggg gcggggcgag    5220
gcggagaggt gcggcggcag ccaatcagag cggcgcgctc cgaaagtttc cttttatggc    5280
gaggcggcgg cggcggcgc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg cgcagcgctg ccacgtcaga cgaagggcgc agcgagcgtc    5520
ctgatccttc cgcccgacg ctcaggacag cggcccgctc ctcataagac tcggccttag    5580
aaccccagta tcagcagaag gacattttag gacgggactt gggtgactct agggcactgg    5640
ttttctttcc agagagcgga acaggcgagg aaaagtagtc cctcctcggc gattctgcgg    5700
agggatctcc gtggggcggt gaacgccgat gatgcctcta ctaaccatgt tcatgttttc    5760
ttttttttc tacaggtcct gggtgacgaa cagggtaccg ccaccatggc caccgctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgaga    5940
tagttggttg ggtggtctgc gttttggcct ctgactgacg cagaccacca ccaactatct    6000
caggacacaa ggcctgttac tagcactcac atggaacaaa tggcctctag cctggaggct    6060
tgctgaaggc tgtatgctgt gctaatcatc atacggtcac gcgttttggc tctgactga    6120
cgcgtgaccg tgatgattag cacaggacac aaggcctgtt actagcactc acatggaaca    6180
aatgcctct agcctggagg cttgctgaag gctgtatgct gacatagccc agaaccaggt    6240
aaacgttttg gcctctgact gacgtttacc tggctgggct atgtcaggac acaaggcctg    6300
ttactagcac tcacatggaa caaatggcct ctctagaat                          6339
```

SEQ ID NO: 8           moltype = DNA   length = 6339
FEATURE                Location/Qualifiers
source                 1..6339
                       mol_type = other DNA
                       organism = synthetic construct
SEQUENCE: 8

```
aatcaacctc tggattacaa aatttgtgaa agattgactg gtattcttaa ctatgttgct      60
cctttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttc tcaggcaacg tggcgtggtg tgcactgtgt ttgctgacgc aaccccact     240
ggttggggca ttgccaccac ctgtcagctc ctttccggta cttcgcttt cccctcact     300
attgccacgg cggaactcat cgccgcctgc cttgcccgct gctgacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccgctc tgcggcctc tccgcgtctt     540
cgccttcgcc ctcagacgag tcggatctc ctttgggccg cctccccgcc taagcttatc     600
gataccgtcg agatcaact tgtttattgc agcttataat ggttacaaat aaagcaatag     660
catcacaaat ttcacaaata aagcatttt ttcactgcat tctagttgtg gtttgtccaa     720
actcatcaat gtatcttatc atgtctggat ctcgacctcg actagagcat ggctacgtag     780
ataagtagca tggcgggtta atcattaact acaaggaacc cctagtgatg gagttggcca     840
ctccctctct gcgcgctcgc tcgctcactg aggccgggcg accaaaggtc gcccgacgcc     900
cgggctttgc ccgggcggcc tcagtgagcg agcgagcgcg cagctggcgt aatagcgaag     960
aggcccgcac cgatcgccct tcccaacagt tgcgcagcct gaatggcgaa tggcgattcg    1020
gttgcaatgg ctggcggtaa tattgttctg gatattacca caaggccga tagtttgagt    1080
tcttctactc aggcaagtga tgttattact aatcaaagaa gtattgcgac aacgttaat    1140
ttgcgtgatg gacagactct tttactcggt ggcctcactg attataaaa cacttctcag    1200
gattctggcc taccgttcct gtctaaaatc cctttaatcg gcctcctgtt tagctcccgc    1260
tctgattcta cgaggaaag cacgtttatac gtgctcgtca agcaaccat agtacgcgact    1320
ctgtagcgcg gcattaagcg cggcgggtgt ggtggttacg cgcagcgtga ctgctacact    1380
tgccagcgcc ctagcgcccg ctccttttcgc tttcttccct tcctttctcg ccacgttcgc    1440
cggctttccc cgtcaagctc taaatcgggg ctcccttta gggttccgat ttagtgcttt    1500
acggcacctc gaccccaaaa aacttgatta gggtgatggt tcacgtagtg gccatcgcc    1560
ctgatagacg gttttttcgcc ctttgacgtt ggagtccacg ttctttaata gtggactctt    1620
gttccaaact ggaacaacac tcaaccctat ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
gacctctcaa aaatagctac cctctccggc atgaatttat cagctagaac ggttgaatat    1980
```

```
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgttttttgg tacaaccgat 2160
ttagcttttat gctctgaggc tttattgctt aattttgcta attctttgcc ttgcctgtat 2220
gatttattgg atgttggaat tcctgatgcg gtatttcctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaaggcct cgtgatacgc ctattttat aggttaatgt 2520
catgataata atggttct t  agacgtcagg tggcacttttt cggggaaatg tgcgcggaac 2580
ccctatttgt ttattttct  aaatacattc aaatatgtat ccgctcatga acaataacc 2640
ctgataaatg cttcaataat attgaaaaag gaagagtatg agtattcaac atttccgtgt 2700
cgcccttatt ccctttttg  cggcattttg ccttcctgtt tttgctcacc cagaaacgct 2760
ggtgaaagta aaagatgctg aagatcagtt gggtgcagca gtgggttaca tcgaactgag 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
tttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatgaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acgggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg ggggggtcgt gcacacagcc cagcttggag cgaacgacct acaccgaact 4080
gagataccta cagcgtgagc tatgagaaag cgccacgctt cccgaaggga aaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg gcggagcct atggaaaaac gccagcaacg cggccttttt 4320
acggttcctg gccttttgct ggccttttgc tcacatgttc tttcctgcgt tatccctga 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca tgctctagga cattgattat tgactagtgg 4740
agttccgcgt tacataactt acggtaaatg gcccgcctgg ctgaccgccc aacgacccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgccccct attgacgtca atgacggtaa atggcccgcc tggcattatg 4980
cccagtacat gaccttatgg gactttccta cttggcagta catctacgta ttagtcatcg 5040
ctattaccat ggtcgaggtg agccccacgt tctgcttcac tctccccatc tcccccccct 5100
ccccacccc aattttgtat ttatttatt tttaattatt ttgtgcagcg atgggggcgg 5160
gggggggggg gggcgcgcgc caggcggggc gggcggggc gaggggcggg gcggggcgag 5220
gcggagaggt gcggcgcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgccccgtgc cccgctccgc cgccgcctcg cgccgcccgc cccggctctg 5400
actgaccgcg ttactaaaac aggtaagtcc ggcctccgcg ccgggttttg gcgcctcccg 5460
cgggcgcccc cctcctcacg gcgagcgctg ccacgtcaga cgaagggcgc agcgagcgtc 5520
ctgatccttc cgcccgacg ctcaggacag cggcccgctg ctcataagac tcggccttag 5580
aaccccagta tcagcagaag gacatttag gacgggactt gggtgactct agggcactgg 5640
ttttctttcc agagagcgga acaggcgagg aaaagtagtc cctttctcggc gattctgcgg 5700
agggatctcg tgggcggt gaacgccgat gatgcctcta ctaaccatgt tcatgttttc 5760
ttttttttttc tacaggtcct gggtgacgaa cagggtaccg ccaccatgc caccggctct 5820
cgcacaagcc tgctgctggc tttcggactg ctgtgcctcc ccttggctcca ggagggctcc 5880
gccgctagca tcgataccgt cgctatgtgc tggaggcttg ctgaaggctg tatgctgaga 5940
tagttggttg ggtggtctgc gttttggcct ctgactgacg cagaccacca ccaactatct 6000
caggacacaa ggcctgttac tagcactcac atggaacaaa tggcctctag cctggaggct 6060
tgctgaaggc tgtatgctgt ttcttcgcgt tgttcagttc gcgttttggc tctgactgca 6120
cgcgaactga aacgcgaaga aacaggacac aaggcctgtt actagcactc acatggaaca 6180
aatgcctct agcctggagg cttgctgaag gctgtatgct gtttcttcgc gtaattcagt 6240
tcgcgttttg gcctctgact gacgcgaact gaaacgcgaa gaaacaggac acaaggcctg 6300
ttactagcac tcacatggaa caaatggcct ctctagaat                        6339
```

| SEQ ID NO: 9 | moltype = DNA length = 6339 |
|---|---|
| FEATURE | Location/Qualifiers |
| source | 1..6339 |
| | mol_type = other DNA |
| | organism = synthetic construct |

```
SEQUENCE: 9
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggccgttg tcaggcaacg tggcgtggtg tgcactgtgt ttgctgacgc aaccccact    240
ggttggggca ttgccaccac ctgtcagctc ctttccggga cttcgctttt ccccctcct    300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttcg gctacgtccc ttcggccctc   480
aatccagcgg accttcctc ccgcggcctg ctgccggctc tgcggcctct tccgcgtcct    540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaggtc gcccgacgcc    900
cgggctttgc ccgggcggcc tcagtgagcg agcgagcgcg cagctggcgt aatagcgaag   960
aggcccgcac cgatcgccct tcccaacagt tgcgcagcct gaatgcgaa tggcgattcc    1020
gttgcaatgg ctggcggtaa tattgttctg gatattacca gcaaggccga tagtttgagt  1080
tcttctactc aggcaagtga tgttattact aatcaaagaa gtattgcgac aacgttaat    1140
ttgcgtgatg gacagactct tttactcggt ggcctcactg attataaaaa cacttctcag  1200
gattctggcg taccgttcct gtctaaaatc cctttaatcg gcctcctgtt tagctcccgc  1260
tctgattcta acgaggaaag cacgttatac gtgctcgtca aagcaaccat agtacgcgcc  1320
ctgtagcggc gcattaagcg cggcgggtgt ggtggttacg cgcagcgtga ccgctacact  1380
tgccagcgcc ctagcgcccg ctcctttcgc tttcttccct tcctttctcg ccacgttcgc  1440
cggctttccc cgtcaagctc taaatcgggg gctcccttta gggttccgat ttagtgcttt  1500
acggcacctc gaccccaaaa aacttgatta gggtgatggt tcacgtagtg gccatcgcc   1560
ctgatagacg gttttttcgcc ctttgacgtt ggagtccacg ttctttaata gtggactctt  1620
gttccaaact ggaacaacac tcaacccat ctcggtctat tcttttgatt tataagggat   1680
tttgccgatt tcggcctatt ggttaaaaaa tgagctgatt taacaaaaat ttaacgcgaa  1740
ttttaacaaa atattaacgt ttacaattta aatatttgct tatacaatct tcctgttttt  1800
ggggcttttc tgattatcaa ccggggtaca tatgattgac atgctagttt tacgattacc  1860
gttcatcgat tctcttgttt gctccagact ctcaggcaat gacctgatag cctttgtaga  1920
gacctctcaa aaatagctac cctctccggc atgaattat cagctagaac ggttgaatat   1980
catattgatg gtgatttgac tgtctccggc ctttctcacc cgtttgaatc tttacctaca  2040
cattactcag gcattgcatt taaaatatat gagggttcta aaaattttta tccttgcgtt  2100
gaaataaagg cttctcccgc aaaagtatta cagggtcata atgttttgg tacaaccgat   2160
ttagctttat gctctgaggc tttattgctt aattttgcta attcttgcc ttgcctgtat   2220
gatttattgg atgttgaat tcctgatgcg gtattttctc cttacgcatc tgtgcggtat  2280
ttcacaccgc atatggtgca ctctcagtac aatctgctct gatgccgcat agttaagcca  2340
gccccgacac ccgccaacac ccgctgacgc gccctgacgg gcttgtctgc tcccggcatc  2400
cgcttacaga caagctgtga ccgtctccgg gagctgcatg tgtcagaggt tttcaccgtc  2460
atcaccgaaa cgcgcgagac gaaaggcct cgtgatacgc ctatttttat aggttaatgt   2520
catgataata atggtttctt agacgtcagg tggcacttt cggggaaatg tgcgcggaac   2580
ccctatttgt ttatttttct aaatacattc aaatatgtat ccgctcatga acaataacc   2640
ctgataaatg cttcaataat attgaaaaag gaagagtatg agtattcaac atttccgtgt  2700
cgcccttatt cccttttttg cggcattttg ccttcctgtt tttgctcacc cagaaacgct  2760
ggtgaaagta aaagatgctg aagatcagtt gggtgcacga gtgggttaca tcgaactgga  2820
tctcaacagc ggtaagatcc ttgagagttt tcgccccgaa gaacgttttc caatgatgag  2880
cacttttaaa gttctgctat gtggcgcggt attatcccgt attgacgccg ggcaagagca  2940
actcggtcgc cgcatacact attctcagaa tgacttggtt gagtactcac cagtcacaga  3000
aaagcatctt acggatgca tgacagtaag agaattatgc agtgctgcca taaccatgag   3060
tgataacact gcggccaact tacttctgac aacgatcgga ggaccgaagg agctaaccgc  3120
ttttttgcac aacatggggg atcatgtaac tcgccttgat cgttgggaac cggagctgaa  3180
tgaagccata ccaaacgacg agcgtgacac cacgatgcct gtagcaatgg caacaacgtt  3240
gcgcaaacta ttaactggcg aactacttac tctagcttcc cggcaacaat taatagactg  3300
gatgaggcg gataaagttg caggaccact tctgcgctcg gcccttccgg ctggctggtt   3360
tattgctgat aaatctggag ccggtgagcg tgggtctcgc ggtatcattg cagcactggg  3420
gccagatggt aagccctccc gtatcgtagt tatctacacg acggggagtc aggcaactat  3480
ggatgaacga aatagacaga tcgctgagat aggtgcctca ctgattaagc attggtaact  3540
gtcgaccaa gtttactcat atatacttta gattgattta aaacttcatt tttaatttaa   3600
aaggatctag gtgaagatcc ttttgataa tctcatgacc aaaatccctt aacgtgagtt   3660
ttcgttccac tgagcgtcag accccgtaga aaagatcaaa ggatcttctt gagatccttt  3720
ttttctgcgc gtaatctgct gcttgcaaac aaaaaaacca ccgctaccag cggtggtttg  3780
tttgccggat caagagctac caactctttt tccgaaggta actggcttca gcagagcgca  3840
gataccaaat actgtcttc tagtgtagcc gtagttaggc caccacttca agaactctgt   3900
agcaccgcct acatacctcg ctctgctaat cctgttacca gtggctgctg ccagtggcga  3960
taagtcgtgt cttaccgggt tggactcaag acgatagtta ccggataagg cgcagcggtc  4020
gggctgaacg gggggttcgt gcacacagcc cagcttggag cgaacgacct acaccgaact  4080
gagataccta cagcgtgagc tatgagaaag cgccacgctt cccgaaggga aaaggcgga   4140
caggtatccg gtaagcggca gggtcggaac aggagagcgc acgagggagc ttccaggggg  4200
aaacgcctgg tatctttata gtcctgtcgg gtttcgccac ctctgacttg agcgtcgatt  4260
tttgtgatgc tcgtcagggg gcggagcct atggaaaaac gccagcaacg cggcctttt    4320
acggttcgtg gccttttgct ggccttttgc tcacatgttc tttcctgcgt tatccctga   4380
ttctgtggat aaccgtatta ccgcctttga gtgagctgat accgctcgcc gcagccgaac  4440
gaccgagcgc agcgagtcag tgagcgagga agcggaagag cgcccaatac gcaaaccgcc  4500
tctccccgcg cgttggccga ttcattaatg cagcagctgc gcgctcgctc gctcactgag  4560
gccgcccggg caaagcccgg gcgtcgggcg acctttggtc gcccggcctc agtgagcgag  4620
cgagcgcgca gagagggagt ggccaactcc atcactaggg gttccttgta gttaatgatt  4680
```

-continued

```
aacccgccat gctacttatc tacgtagcca tgctctagga cattgattat tgactagtgg  4740
agttccgcgt tacataactt acggtaaatg gcccgcctgg ctgaccgccc aacgaccccc  4800
gcccattgac gtcaataatg acgtatgttc ccatagtaac gccaatagg actttccatt  4860
gacgtcaatg ggtggagtat ttacggtaaa ctgcccactt ggcagtacat caagtgtatc  4920
atatgccaag tacgccccct attgacgtca atgacggtaa atggcccgcc tggcattatg  4980
cccagtacat gaccttatgg gactttccta cttggcagta catctacgta ttagtcatcg  5040
ctattaccat ggtcgaggtg agccccacgt tctgcttcac tctccccatc tcccccccct  5100
ccccacccc aattttgtat ttatttattt tttaattatt ttgtgcagcg atggggggcgg  5160
ggggggggg gggcgcgcgc caggcggggc ggggcggggc gaggggcggg gcggggcgag  5220
gcggagaggt gcggcggcag ccaatcagag cggcgcgctc cgaaagtttc cttttatggc  5280
gaggcggcgg cggcggcggc cctataaaaa gcgaagcgcg cggcgggcgg gagtcgctgc  5340
gcgctgcctt cgccccgtgc cccgctccgc cgccgcctcg cgccgcccgc cccggctctg  5400
actgaccgcg ttactaaaac aggtaagtcc ggcctccgcg ccgggttttg gcgcctcccg  5460
cgggcgcccc cctcctcacg gcgagcgctg ccacgtcaga cgaagggcgc agcgagcgtc  5520
ctgatccttc cgcccggacg ctcaggacag cggcccgctg ctcataagac tcggccttag  5580
aaccccagta tcagcagaag gacattttag gacgggactt gggtgactct agggcactgg  5640
ttttctttcc agagagcgga acaggcgagg aaaagtagtc ccttctcggc gattctgcgg  5700
agggatctcc gtggggcggt gaacgccgat gatgcctcta ctaaccatgt tcatgttttc  5760
ttttttttc tacaggtcct gggtgacgaa cagggtaccg ccaccatggc caccggctct  5820
cgcacaagcc tgctgctggc tttcggactg ctgtgcctgc cttggctcca ggagggctcc  5880
gccgctagca tcgataccgt cgctatgtgc tggaggcttg ctgaaggctg tatgctgata  5940
aatcaccgtg ggttcagcgc gttttggcct ctgactgacg cgttcgaaccc ggtgatttat  6000
caggacacaa ggcctgttac tagcactcac atggaacaaa tggcctctag cctggaggct  6060
tgctgaaggc tgtatgctga taaatcaccg atggttcagc gcgttttggc ctctgactga  6120
cgcgctgaac ccggtgattt atcaggacac aaggcctgtt actagcactc acatggaaca  6180
aatggcctct agcctggagg cttgctgaag gctgtatgct gataaatcac cgaaggttca  6240
gcgcgttttg gcctctgact gacgcgctga acccggtgat ttatcaggac acaaggcctg  6300
ttactagcac tcacatggaa caaatggcct ctctagaat                          6339
```